US010076264B2

(12) United States Patent
Brady-Kalnay et al.

(10) Patent No.: US 10,076,264 B2
(45) Date of Patent: Sep. 18, 2018

(54) SYSTEM AND METHOD FOR QUANTITATIVE MAGNETIC RESONANCE (MR) ANALYSIS USING T1 MAPPING

(71) Applicant: Case Western Reserve University, Cleveland, OH (US)

(72) Inventors: Susann Brady-Kalnay, Cleveland, OH (US); Vikas Gulani, Cleveland, OH (US); Mark Griswold, Shaker Heights, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/169,208

(22) Filed: May 31, 2016

(65) Prior Publication Data

US 2016/0270687 A1 Sep. 22, 2016

Related U.S. Application Data

(63) Continuation-in-part of application No. 14/068,537, filed on Oct. 31, 2013, now Pat. No. 9,508,256.

(Continued)

(51) Int. Cl.

*A61B 5/055* (2006.01)
*G01R 33/56* (2006.01)

(Continued)

(52) U.S. Cl.

CPC ............ *A61B 5/055* (2013.01); *A61B 5/0073* (2013.01); *A61B 5/4244* (2013.01); *A61B 5/742* (2013.01);

(Continued)

(58) Field of Classification Search

CPC ..... A61B 5/055; A61B 5/0073; A61B 5/4244; A61B 5/742; A61B 2576/00;

(Continued)

(56) References Cited

U.S. PATENT DOCUMENTS

| | | | |
|---|---|---|---|
| 7,319,784 | B2 | 1/2008 | Ryner et al. |
| 8,723,518 | B2 | 5/2014 | Seiberlich et al. |

(Continued)

OTHER PUBLICATIONS

Akeson, et al., Time-Dependency in Brain Lesion Enhancement with Gadodiamide Injection, Acta Radiologica, 1997, 38:19-24.

(Continued)

*Primary Examiner* — Gregory H Curran
(74) *Attorney, Agent, or Firm* — Quarles & Brady LLP

(57) ABSTRACT

Example apparatus and methods concern determining whether a target material appears in a region experiencing nuclear magnetic resonance (NMR). One method acquires a baseline value for a magnetic resonance parameter (MRP) while the region is not exposed to a molecular imaging agent that affects the MRP and acquires a series of quantitative values for the MRP while the sample is influenced by a molecular imaging agent. Quantitative values may be acquired during a clinically relevant time period (e.g., 60 minutes) during which the change in the MRP (e.g., T1) caused by the molecular imaging agent is at least 90% of the peak change caused by the molecular imaging agent. The molecular imaging agent may be SBK2 and may produce a desired change in T1 for at least thirty minutes in glioblastoma.

58 Claims, 27 Drawing Sheets
(11 of 27 Drawing Sheet(s) Filed in Color)

Related U.S. Application Data

(60) Provisional application No. 61/806,907, filed on Mar. 31, 2013, provisional application No. 62/167,946, filed on May 29, 2015, provisional application No. 62/187,961, filed on Jul. 2, 2015, provisional application No. 62/212,417, filed on Aug. 31, 2015.

(51) Int. Cl.

| | |
|---|---|
| ***A61B 5/00*** | (2006.01) |
| ***A61K 49/10*** | (2006.01) |
| ***G08C 23/06*** | (2006.01) |
| ***G01R 33/50*** | (2006.01) |

(52) U.S. Cl.
CPC ............ *A61K 49/108* (2013.01); *G01R 33/50* (2013.01); *G01R 33/5601* (2013.01); *G01R 33/5602* (2013.01); *G08C 23/06* (2013.01); *A61B 2576/00* (2013.01); *A61B 2576/026* (2013.01)

(58) Field of Classification Search
CPC ............ A61B 2576/026; A61K 49/108; G01R 33/50; G01R 33/5601; G01R 33/5602; G08C 23/06
See application file for complete search history.

(56) References Cited

U.S. PATENT DOCUMENTS

| | | | | |
|---|---|---|---|---|
| 9,113,800 | B2 | 8/2015 | Schmidt | |
| 9,508,256 | B2 | 11/2016 | Brady-Kalnay et al. | |
| 2008/0044358 | A1 | 2/2008 | Jacques et al. | |
| 2010/0160173 | A1 | 6/2010 | Mchale et al. | |
| 2011/0171122 | A1 | 7/2011 | Brady-Kalnay | |
| 2013/0265047 | A1* | 10/2013 | Griswold ............... | G01R 33/56 324/309 |
| 2013/0287702 | A1 | 10/2013 | Brady-Kalnay | |
| 2014/0178299 | A1 | 6/2014 | Brady-Kalnay | |
| 2015/0099964 | A1* | 4/2015 | Voigt ................... | A61B 5/7292 600/420 |
| 2016/0083734 | A1 | 3/2016 | Brady-Kalnay | |

OTHER PUBLICATIONS

Ali, et al., A Nano-Sized Paracest-fluorescence Imaging Contrast Agent Facilitates & Validates in Vivo CEST MRI Detection of Glioma, Nanomedicine (Lond), 2012, 7(12):1827-1837.
Bae, et al., Targeted Drug Delivery to Tumors: Myths, Reality and Possibility, J. Control Release, 2011, 153 (3):198-205.
Bertrand, et al., Cancer Nanotechnology: The Impact of Passive and Active Targeting in the Era of Modern Cancer Biology, Adv. Drug Deliv. Rev., 2014, 66:2-25.
Burden-Gulley, et al., A Novel Molecular Diagnostic of Glioblastomas: Detection of an Extracellular Fragment of ProteinTyrosine Phosphatase mu, Neoplasia, 2010, 12(4):305-316.
Burden-Gulley, et al., Novel Cryo-Imaging of the Glioma Tumor Microenvironment Reveals Migration and Dispersal Pathways in Vivid Three-Dimensional Detail, Cancer Research, 2011, 71(17):5932-5940.
Burden-Gulley, et al., Single Cell Molecular Recognition of Migrating and Invading Tumor Cells Using a Targeted Fluorescent Probe to Receptor PTPmu, Int. J. Cancer, 2013, 132(7):1624-1632.
Burden-Gulley, et al., Molecular Magnetic Resonance Imaging of Tumors with a PTPmu Targeted Contrast Agent, Translational Oncology, 2013, 6(3):329-337.
Burgoyne, et al., Proteolytic Cleavage of Protein Tyrosine Phosphatase mu Regulates Glioblastoma Cell Migration, Cancer Research, 2009, 69(17):6960-6968.
Coolen, et al., Regional Contrast Agent Quantification in a Mouse Model of Myocardial Infarction Using 3D Cardiac T1 Mapping, Journal of Cardiovascular Magnetic Resonance, 2011, 13:56, 9 pages.
Coquery, et al., Microvascular MRI and Unsupervised Clustering Yields Histology-Resembling Images in Two Rat Models of Glioma, Journal of Cerebral Blood Flow & Metabolism, 2014, 34:1354-1362.
Deichmann, et al., Quantification of T1 Values by Snapshot-Flash NMR Imaging, Journal of Magnetic Resonance, 1992, 96:608-612.
Furnari, et al., Malignant Astrocytic Glioma: Genetics, Biology, and Paths to Treatment, Genes & Development, 2007, 21:2683-2710.
Gan, et al., The Epidermal Growth Factor Receptor Variant III (EGFRvIII): Where Wild Things Are Altered, FEBS Journal, 2013, 280:5350-5370.
Geraldes, et al., Classification and Basic Properties of Contrast Agents for Magnetic Resonance Imaging, Contrast Media Mol. Imaging, 2009, 4:1-23.
Hennig, et al., Rare Imaging: A Fast Imaging Method for Clinical MR, Magnetic Resonance in Medicine, 1986, 3 (6):823-833.
Herrmann, et al., Molecular Imaging of Tumors Using a Quantitative T1 Mapping Technique Via Magnetic Resonance Imaging, Diagnostics, 2015, 5:318-332.
Iacob, et al., Current Data and Strategy in Glioblastoma Multiforme, Journal of Medicine and Life, 2009, 2(4):386-393.
Ichimura, et al., Molecular Pathogenesis of Astrocytic Tumours, Journal of Neuro-Oncology, 2004, 70(2):137-160.
Jakob, et al., Rapid Quantitative Lung 1H T1 Mapping, Journal of Magnetic Resonance Imaging, 2001, 14:795-799.
Kircher, et al., Molecular Body Imaging: MR Imaging, CT, and US. Part I. Principles, Radiology, 2012, 263 (3):633-643.
Kohler, et al., Annual Report to the Nation on the Status of Cancer, 1975-2007, Featuring Tumors of the Brain and Other Nervous System, J. Natl. Cancer Inst., 2011, 103:714-736.
Lescher, et al., Quantitative T1 and T2 Mapping in Recurrent Glioblastomas Under Bevacizumab: Earlier Detection of Tumor Progression Compared to Conventional MRI, Neuroradiology, 2015, 57(1):11-20.
Louis, et al., The 2007 WHO Classification of Tumours of the Central Nervous System, Acta Neuropathol., 2007, 114:97-109.
Ma, et al., Magnetic Resonance Fingerprinting, Nature, 2013, 495(7440):187-192.
Maeda, Toward a Full Understanding of the EPR Effect in Primary and Metastatic Tumors As Well As Issues Related to Its Heterogeneity, Adv. Drug Deliv. Rev., 2015, 91:3-6.
Mastarone, et al., A Modular System for the Synthesis of Multiplexed Magnetic Resonance Probes, J. Am. Chem. Soc., 2011, 133(14):5329-5337.
Nomoto, Brain Metastasis of Small Cell Lung Carcinoma: Comparison of Gd-DTPA Enhanced Magnetic Resonance Imaging and Enhanced Computerized Tomography, Japanese Journal of Clinical Oncology, 1994, 24(5):258-262.
Rose, et al., Quantifying Spatial Heterogeneity in Dynamic Contrast-Enhanced MRI Parameter Maps, Magnetic Resonance in Medicine, 2009, 62:488-499.
Runge, et al., High-Dose Gadoteridol in MR Imaging of Intracranial Neoplasms, Journal of Magnetic Resonance Imaging, 1992, 2(1):9-18.
Sagiyama, et al., In Vivo Chemical Exchange Saturation Transfer Imaging Allows Early Detection of a Therapeutic Response in Glioblastoma, PNAS, 2014, 111(12):4542-4547.
Sanai, et al., An Extent of Resection Threshold for Newly Diagnosed Glioblastomas, J. Neurosurg., 2011, 115:3-8.
Stupp, et al., Radiotherapy Plus Concomitant and Adjuvant Temozolomide for Glioblastoma, The New England Journal of Medicine, 2005, 352:987-996.
Sun, et al., Perfusion MRI of U87 Brain Tumors in a Mouse Model, Magnetic Resonance in Medicine, 2004, 51:893-899.
Tyagi, et al., CBF-1 Promotes Transcriptional Silencing During the Establishment of HIV-1 Latency, The EMBO Journal, 2007, 26:4985-4995.
Tyminski, et al., Brain Tumor Oncolysis with Replication-Conditional Herpes Simplex Virus Type 1 Expressing the Prodrug-Activating Genes, CYP2B1 and Secreted Human Intestinal

(56) References Cited

OTHER PUBLICATIONS

Carboxylesterase, in Combination With Cyclophosphamide and Irinotecan, Cancer Research, 2005, 65(15):6850-6857.
Upadhyay, et al., Conventional MRI Evaluation of Gliomas, The British Journal of Radiology, 2011, 84:S107-S111.
Wen, et al., Updated Response Assessment Criteria for High-Grade Gliomas: Response Assessment in Neuro-Oncology Working Group, Journal of Clinical Oncology, 2010, 28(11):1963-1972.
Yousry, et al., Visualization of Cranial Nerves I-XII: Value of 3D CISS and T2-Weighted FSE Sequences, European Radiology, 2000, 10(7):1061-1067.
Yuh, et al., Phase III Multicenter Trial of High-Dose Gadoteridol in MR Evaluation of Brain Metastases, AJNR Am. J. Neuroradiol., 1994, 15:1037-1051.
Yuh, et al., Delineation of Gliomas With Various Doses of MR Contrast Material, AJNR Am. J. Neuroradiol., 1994, 15:983-989.
Yuh, et al., MR Evaluation of CNS Tumors: Dose Comparison Study with Gadopentetate Dimeglumine and Gadoteridol, RSNA Radiology, 1991, 180(2):485-491.
Zhou, et al., Peptide Targeted Tripod Macrocyclic Gd(III) Chelates for Cancer Molecular MRI, Biomaterials, 2013, 34 (31):7683-7693.

* cited by examiner

SYSTEM AND METHOD FOR QUANTITATIVE MAGNETIC RESONANCE (MR) ANALYSIS USING T1 MAPPING

PRIORITY CLAIM

This application is a continuation in part of U.S. patent application Ser. No. 14/068,537, titled "Magnetic Resonance Imaging (MRI) With Dual Agent Characterization", filed Oct. 31, 2013, which claims priority to U.S. Provisional Application 61/806,907, titled "Medical Imaging", filed Mar. 31, 2013. This application claims priority to U.S. Provisional Application 62/167,946 titled "Molecular Imaging of Tumors Using Quantitative T1 Mapping", filed May 29, 2015 and incorporated herein by reference. This application claims priority to U.S. Provisional Application 62/187,961 titled "Molecular Imaging of Tumors Using Quantitative T1 Mapping", filed Jul. 2, 2015 and incorporated herein by reference. This application claims priority to U.S. Provisional Application 62/212,417 titled "Quantitative T1 Mapping of Brain Tumors", filed Aug. 31, 2015 and incorporated herein by reference.

FEDERAL FUNDING NOTICE

The invention was made with government support under Federal Grant No. R01 CA 179956 awarded by National Institutes of Health. The government has certain rights in the invention.

BACKGROUND

Magnetic resonance imaging (MRI) is used to diagnose a variety of cancers, including brain tumors. MRI, nuclear magnetic resonance (NMR), and other magnetic resonance (MR) apparatus, systems, and approaches continue to become more sophisticated, powerful, precise, and complicated. However, MRI continues to experience limits in image resolution due to hard physical and physiological limits. These physical realities have limited conventional systems to imaging tumors that are larger than 10 mm in diameter. Conventionally, T1-weighted images have been used by clinicians to assess brain abnormalities. However, these conventional assessments have been of limited value because conventional T1-weighted images and T2-weighted images are non-quantitative and their interpretation is necessarily subjective. Additionally, conventional T1 weighted and T2 weighted images have had inadequate resolution to detect very small tumors (e.g., less than 2 mm in diameter). T1 refers to spin-lattice relaxation and T2 refers to spin-spin relaxation.

MR involves the transmission of carefully controlled radio frequency (RF) energy in the presence of carefully controlled magnetic fields to produce NMR in a material exposed to the RF energy. Increasing the strength of the magnetic fields used in MRI to, for example, 7 T improves spatial resolution but reduces contrast. Thus, contrast agents have been employed to attempt to increase contrast. As the magnetic field is strengthened, higher frequencies are needed for the radio frequency (RF) to produce NMR because of the Larmor relationship:

$$\omega=\gamma B_0$$

where:

$\omega$ is the precession frequency $\gamma$ is the gyromagnetic ratio, and $B_0$ is the magnetic field strength.

Unfortunately, the higher frequencies used with the higher magnetic field strength also reduce the effectiveness of the conventional contrast agents used in MRI. For example, a contrast agent that produces a first change in T1 in a lower strength field may produce a second, lower change in T1 in a higher strength field.

Due to the physical and physiological limits, conventional 1.5 T or 3 T human scanners have typically been limited to a resolution of approximately 2×2×2 $mm^3$. However, some targets to be evaluated using MRI (e.g., tumors, groups of cancer cells, individual cancer cells, proteins) may be significantly smaller than 2×2×2 $mm^3$. For example, some tumor cells may be as small as 10 microns.

While various imaging modalities are used in clinical and surgical settings, MRI is a preferred method of brain tumor imaging prior to surgery. Conventionally, even though an NMR signal may have been acquired from a tumor or cancer cell that was less than the voxel size used in MR acquisition and reconstruction, it has been difficult, if even possible at all, to distinguish those voxels from voxels that do not include small targets. Targeted molecular contrast agents have facilitated improving the MRI assessment of tumors. However, the usefulness of conventional molecular contrast agents has been limited due to the masking effect of nonspecific uptake or due to the limited time during which changes in contrast due to the molecular contrast agent are present.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

The patent or application file contains at least one drawing executed in color. Copies of this patent or patent application publication with color drawing(s) will be provided by the Office upon request and payment of the necessary fee.

DETAILED DESCRIPTION

Figure 1:
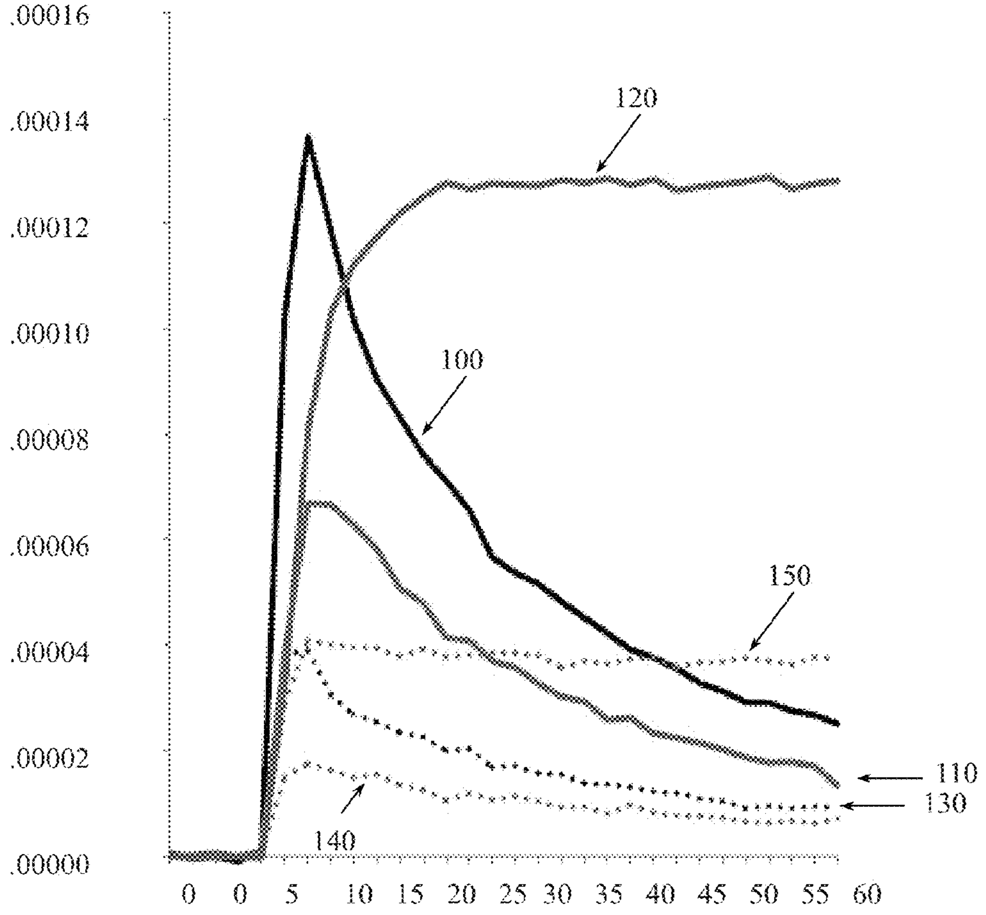
FIG. 1 illustrates plots of Gd concentrations over time.

Example apparatus and methods use quantitative MR systems and analysis with T1 relaxation time mapping to image tumors (e.g., glioblastoma) down to 1 mm in diameter. T1 relaxation time mapping is used to compare changes in T1 relaxation time over time in a material due to the presence of a molecular imaging agent. The molecular imaging agent causes a contrast agent to accumulate in the material (e.g., tumor) and to be retained for a clinically relevant period of time (e.g., 30 minutes). The contrast agent changes the T1 relaxation time. The amount by which the contrast agent changes the T1 relaxation time corresponds directly with the concentration of contrast agent in the material. T1 relaxation time mapping is used to quantitatively determine contrast agent concentration in a material (e.g., tumor) over time to identify initial changes in T1 and longer term changes in T1 responses due to imaging agent retention, which may in turn facilitate improved tumor imaging and identifying a disease state. T1 relaxation time mapping produces a quantitative result that identifies contrast agent percentage, whereas T1-weighted imaging produces an image that is subjectively evaluated to produce a qualitative result. The quantitative value facilitates making an objective determination based on the quantitative values.

Different molecular imaging agents may be employed. For example, imaging agents including Optimark™, Prohance™, and SBK2 may be employed. Optimark™ (gadoversetamide) and Prohance™ (gadoteridol) are examples of non-specific molecular imaging agents. SBK2 is an example of a specific molecular imaging agent. Non-specific and specific molecular imaging agents may cause different results on T1 relaxation time. Consider two molecular imaging agents that have different sensitivities to recognizing fragments of a protein (e.g., protein tyrosine phosphatase mu (PTPμ)) associated with a certain type of cancer (e.g., glioblastoma). The two molecular imaging agents may initially produce similar to identical effects on an MR parameter (e.g., T1). The initial effect may be due to the passive diffusion of a contrast agent (e.g., Gd-chelates) into tumor tissue. While the initial effect may be similar, the long term effect may be different because one of the molecular imaging agents may bind to the target in a protein:protein interaction which may reduce the rate at which the molecular imaging agents are cleared from the regions into which they were taken up. This binding may allow the concentration of the contrast agent to be higher and to remain high for a clinically relevant period of time (e.g., thirty minutes). The binding may also allow the contrast agent to be spread throughout the tumor, rather than just at its margins or in areas of abnormal blood vessels.

Glioblastoma multiforme (GBM) is a highly aggressive tumor that arises in the brain. GBM exhibits highly dispersive and invasive tumor cells that infiltrate the brain and migrate away from the tumor mass. The distant, migratory cells may be undetectable with conventional MR methods. The receptor protein tyrosine phosphatase PTPμ is a transmembrane protein that is proteolyzed in tumor tissue to yield an extracellular fragment and a membrane-freed intracellular fragment. The proteolyzed extracellular fragment of PTPμ accumulates in aggressive GBM tumors and provides a detectable moiety for molecular imaging.

Different areas may take up different molecular imaging agents in different ways. For example, a specific molecular imaging agent like SBK2 may be taken up by a greater percentage of a tumor and thus may affect the signal in all parts of the tumor while a non-specific molecular imaging agent may be taken up by a smaller percentage of a tumor, or only by a portion (e.g., leaky edge) of a tumor, and thus may affect the signal in only a portion of the tumor. Non-specific molecular imaging agents may produce contrast enhancement on or near a tumor due to the leakage of gadolinium (Gd) out of abnormal vasculature into the extracellular space in a tumor. Acquiring signal from a volume after a non-specific molecular imaging agent has been applied may provide a first set of information. Acquiring signal from the same volume after a specific molecular imaging agent has been applied may provide a second, different set of information. Comparing the two sets of information may facilitate providing a richer data set than using just one or the other molecular imaging agent. For example, subtracting the first set of information from the second set of information may facilitate clarifying tumor boundaries or tumor mass.

Specific molecular imaging agents may be taken up by a tumor more than non-specific molecular imaging agents. For example, SBK2-Tris-(Gd-DOTA)$_3$ accumulates at about twice the concentration of scrambled-Tris-(Gd-DOTA)$_3$ in tumors containing the PTPμ fragment. Specific molecular imaging agents may exhibit nearly identical non-specific uptake as non-specific molecular imaging agents. For example, SBK2-Tris-(Gd-DOTA)$_3$ exhibits nearly identical non-specific uptake as scrambled-Tris-(Gd-DOTA)$_3$. Other non-specific molecular imaging agents (e.g., Prohance™, Optimark™) are also taken up differently than SBK2.

Specific molecular imaging agents may have different clearance rates from a tumor. For example, SBK2-Tris-(Gd- $DOTA)_3$ and scrambled-Tris-$(Gd\text{-}DOTA)_3$ have significantly different clearance rates from the tumor. In particular, SBK2-Tris-$(Gd\text{-}DOTA)_3$ remains in the tumor much longer (e.g., 1 hour) than non-specific molecular imaging agents. Other non-specific molecular imaging agents (e.g., Prohance™, Optimark™) also clear more quickly than SBK2.

FIG. 1 illustrates Gd concentrations in tumor and muscle for three mice. Gd based MR imaging contrast agents shorten the T1 relaxation time and alter the T1 values differently in different tissues (e.g., tumor, muscle). The decrease in T1 relaxation time is directly proportional to the concentration of Gd in the tissue. Using the absolute T1 values in a material (e.g., brain, brain tumor) before and after the presentation of a contrast agent to the volume facilitates acquiring an objective quantitative measurement of contrast agent concentration per voxel of the material. Line 100 illustrates Gd concentration in tumor with Optimark, 0.2 mmol Gd/kg. Line 110 illustrates Gd concentration in tumor with Scram-tris[(Gd-DOTA)3], 0.2 mmol Gd/kg. Line 120 illustrates Gd concentration in tumor with SBK2-tris[(GD-DOTA)3], 0.2 mmol Gd/kg. Line 130 illustrates Gd concentration in muscle with Optimark, 0.2 mmol Gd/kg. Line 140 illustrates Gd concentration in muscle with Scram-tris [(Gd-DOTA)3], 0.2 mmol Gd/kg. Line 150 illustrates Gd concentration in muscle with SBK2-tris[(GD-DOTA)3], 0.2 mmol Gd/kg. In both muscle and tumor, Gd concentration reaches a peak then diminishes over time. The peak is retained for a measurably different period of time for SBK2 as illustrated by lines 120 and 150. Thus, in one embodiment, various types of NMR acquisitions including T1 mapping, T2 weighted, proton density, and MRF may be performed during the lengthy (e.g., 60 minutes) period of time where the change in T1 due to the presence of SBK2 remains above 90% of the peak change.

Example apparatus and methods take advantage of the fact that SBK2 produces a longer term effect on T1. Examining the time course of T1 signals produced by a sample facilitates understanding and quantifying a specific characterization (e.g., diagnosis, phenotyping) of a material exposed to the molecular imaging agent, and in particular to SBK2-Tris-$(Gd\text{-}DOTA)_3$. For example, it may be possible to distinguish voxels that contain small amounts of a target material (e.g., tumor, protein, protein associated with tumor, biological material associated with pathology) from voxels that do not contain the target material based on the retention rate of SBK2 and the corresponding T1 time course.

As used herein, "SBK2" refers to a peptide that is described in: Burden-Gulley S M, Qutaish M Q, Sullivant K E, Tan M, Craig S E, Basilion J P, Lu Z R, Wilson D L, Brady-Kalnay S M. Single cell molecular recognition of migrating and invading tumor cells using a targeted fluorescent probe to receptor PTPmu. Int J Cancer. 2013 Apr. 1; 132(7):1624-32. doi: 10.1002/ijc.27838. Epub 2012 Oct. 11. PubMed PMID: 22987116; PubMed Central PMCID: PMC3558593, and in A Novel Molecular Diagnostic of Glioblastoma: Detection of an Extracellular Fragment of Protein Tyrosine Phosphatase μ, Brady-Kalnay et al., Neoplasia, Volume 12, Number 4, April 2010, pp 305-316; Molecular Magnetic Resonance Imaging of Tumors with a PTPμ Targeted Contrast Agent, Brady-Kalnay et al., Translational Oncology, 2013 Jun. 1; 6(3): 329-37; and in United States Patent Application Publications 2011/0171122; 2016/0083734; 2013/0287702; and 2014/0178299, the contents of all of which are incorporated herein by reference.

Figure 2:
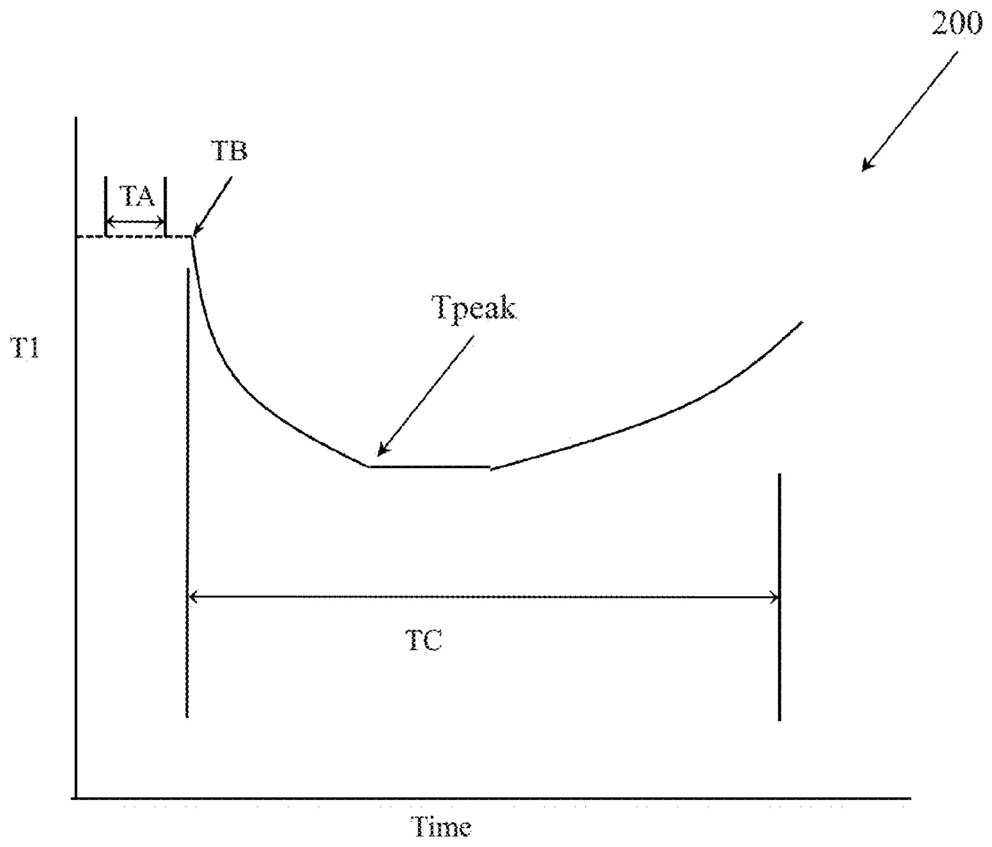
FIG. 2 illustrates a plot of T1 relaxation over time.

FIG. 2 illustrates a timeline associated with one embodiment of a single agent approach. The x axis of graph 200 represents time and the y axis represents T1 of a tissue experiencing NMR. During time interval TA an initial, baseline T1 is measured for a region (e.g., voxel) in a sample. This baseline T1 represents the T1 relaxation of materials in the region without the presence of any T1 altering substances (e.g., contrast agents, Gd-containing molecules). Thus, the baseline T1 data may be referred to as pre-agent data. At time TB, a molecular imaging agent is presented to the sample. In one embodiment, the molecular imaging agent may be just a contrast agent (e.g., Gd-DOTA). In other embodiments, the molecular imaging agent may be a specific agent (e.g., SBK2). During time interval TC, a series of T1 measurements are taken and the change over time in T1 due to the molecular imaging agent is measured and analyzed. While the discrete value for T1 is interesting, the change in T1 between TA and during TC may be more interesting because it can be quantified by converting the change to, for example, a quantitative map. In one embodiment, the quantitative map may provide information about the concentration of the molecular imaging agent. Whether a tissue is cancerous may be determined by the time course of a concentration. For example, if the concentration reaches a pre-defined peak and then stays within 90% of that peak for a pre-determined period of time (e.g., 30 minutes), then the tissue can be characterized as cancerous. Since the time TC may be very long (e.g., up to two hours), other types of measurements may also be acquired. For example, measurements that support T1 weighted imaging, T1 mapping, T2 weighted imaging, T2 mapping, proton density imaging, and magnetic resonance fingerprinting (MRF) may all be performed. MRF is described in U.S. patent application "Nuclear Magnetic Resonance (NMR) Fingerprinting", application Ser. No. 13/051,044, now U.S. Pat. No. 8,723,518 and in *Magnetic Resonance Fingerprinting*, Ma et al., Nature 495, 187-192 (14 Mar. 2013), the contents of both of which are incorporated herein by reference. In one embodiment, a peak change in T1 is identified at time Tpeak. Signal acquisition may continue while T1 remains within a threshold of the signal at Tpeak.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, circuit, processor, or similar electronic device that manipulates and transforms data represented as physical quantities (e.g., electronic values).

Example methods may be better appreciated with reference to flow diagrams. For simplicity, the illustrated methodologies are shown and described as a series of blocks. However, the methodologies may not be limited by the order of the blocks because, in some embodiments, the blocks may occur in different orders than shown and described. More-over, fewer than all the illustrated blocks may be required to implement an example methodology. Blocks may be combined or separated into multiple components. Furthermore, additional or alternative methodologies can employ additional, not illustrated blocks.

Figure 3:
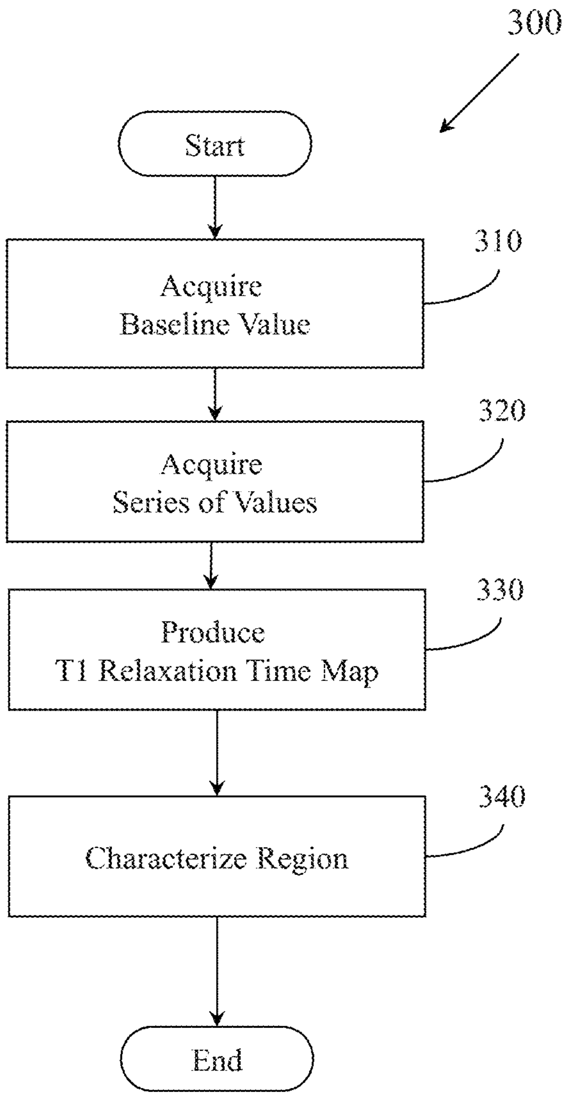
FIG. 3 illustrates a method associated with quantitative MRI using T1 mapping.

FIG. 3 illustrates a method 300. Method 300 includes, at 310, acquiring a pre-agent or baseline value for an MR parameter from a region in a sample while the sample is not exposed to a molecular imaging agent that affects the MR parameter in the sample. The MR parameter may be, for example, T1 relaxation, T2 relaxation, proton density, or some other MR parameter. In one embodiment, the region is bounded by a voxel used in MRI reconstruction. Different region sizes may be employed. In one example, the voxel size is less than 1×1×1 $mm^3$ while in another example the voxel size is greater than or equal to 1×1×1 $mm^3$. Other sizes, including irregular sizes may be employed.

Method 300 also includes, at 320, acquiring a series of values for the MR parameter while the sample is influenced by a molecular imaging agent. The sample may be, for example, a human tissue. Other tissue types (e.g., canine, bovine, equine, feline) and materials may be employed. The target material may be, for example, a protein, a chemical, a peptide, a cancer cell, a disease cell, a cancer marker, a disease marker, or other substance. The MR parameter may be, for example, T1, T2, or proton density. The series of values are acquired using a quantitative mapping approach. Since SBK2 is retained for up to two hours, the series of values may be acquired for a longer period of time compared to conventional systems. In different embodiments, the series of values may be acquired for 15 minutes, 30 minutes, 45 minutes, 60 minutes, 75 minutes, 90 minutes, 120 minutes, or other periods of time. In one embodiment, data from which quantitative T1 maps are produced is collected after a peak in the change in T1 due to the contrast agent is detected and while the change in T1 remains within at least 90% of the peak change.

Method 300 also includes, at 330, producing a quantitative map from the series of values. In one embodiment the MR parameter is T1 relaxation time and the quantitative map is a T1 relaxation time quantitative map. In one embodiment the MR parameter is T2 relaxation time and the quantitative map is a T2 relaxation time quantitative map. In one embodiment the MR parameter is proton density and the quantitative map is a proton density quantitative map. The signals acquired over time are a function of the concentration of the molecular imaging agent in the region. Since the values may represent concentrations, in one example the changes in the MR parameter are quantified by converting the values to concentration maps.

Method 300 also includes, at 340, characterizing the region. Characterizing the region may be a function of the pre-agent or baseline value and the series of values acquired while the sample is influenced by the molecular imaging agent. For example, if the difference between the pre-agent or baseline and a peak signal exceeds a threshold, and if the signal remains within a pre-defined percentage of the peak, then the material may be identified as a tumor. Since the method depends on the sample experiencing controlled NMR, the baseline value and the series of values are a function of magnetic resonance experienced in the sample as excited by an NMR apparatus. The NMR apparatus may employ different approaches including, but not limited to, DESPOT1, MRF, or other MR approaches. Specific uptake of the specific molecular imaging agent (e.g., SBK2) in an area that includes the target material (e.g., tumor) and non-specific uptake of the specific molecular imaging agent (e.g., SBK2) in an area that does not include the target material produce a measurably different effect on the MR parameter in the region. Unlike non-specific agents, SBK2 illustrates dramatically longer retention time in the target. Additionally, SBK2 produces a signal from a larger percentage of the tumor. Since the change in the MR parameter occurs for a longer period of time, additional signal acquisitions that facilitate producing improved signal-to-noise ratio in the data and, thus, improved results or reports, including improved images, is possible.

The specific molecular imaging agent may be configured or chosen to facilitate identifying a specific target. Different targets may be sought. In one example, the target material is a protein associated with a disease. In one example, the target material is a PTPμ fragment associated with cancer (e.g., glioblastoma multiforme). When the target material is a protein, the specific molecular imaging agent may recognize the target material by binding to the target material in a protein:protein interaction. Other mechanisms for recognition that lead to increased concentration of the contrast agent in or near the target material may also be involved. In one embodiment, when the molecular imaging agent is SBK2, the characterization of a region as being a glioblastoma may be made when the concentration of Gd reaches at least 0.08 mM and remains above 0.07 mM for at least 30 minutes. In another embodiment, similar quantitative measurements would be made to distinguish other tumor types.

Method 300 and other methods and apparatus described herein may be more sensitive than conventional systems, in some cases, up to an order of magnitude more sensitive than conventional systems. For example, method 300 and other methods and apparatus described herein may be able to detect a tumor that is less than 1% the size of the region, less than 5% the size of the region, less than 10% of the size of the region, less than 50% the size of the region, or other sizes. In another example, method 300 and other methods and apparatus described herein may be able to detect a change in concentration of less than 250 nM of the contrast agent in the region, of less than 500 nM of the contrast agent in the region, of less than 1000 nM of the contrast agent, or other changes of concentration.

In one embodiment, method 300 may also include controlling a signal detection apparatus to generate a signal or report that indicates that the target material is present in the sample. In one embodiment, the signal or report may identify a phenotype of the target material. The signal or report may also indicate other properties of the sample, target material, or region. For example, the signal or report may indicate that the target material is present in the region. In one embodiment, the signal may be used to control additional processing for the region. For example, if the signal or report indicates that the target material is present in a region, then additional data acquisitions or analysis or different types of data acquisitions or analysis may be employed for the region. Other actions may be taken. The signal or report may be, for example, a visual signal, an audible signal, an electrical signal, a computer interrupt, a procedure call, a voltage on a line, a frequency on a line, or other signal. As used herein, a “report” may include any of a variety of mechanisms for communicating information, including text-based reports, visual signals, or auditory signals or alerts. A report may include the communication of a metric or graphic indicator, or may include images.

In one embodiment, method 300 may also include reconstructing an MR image from NMR received from the sample. The MR image may include information that is a function of the pre-agent or baseline value or the series of values. For example, the MR image may report the initial quantitative values, the difference in quantitative values, or the quantitative values present in the series of values. The image may include information (e.g., T1 relaxation times) concerning the target material (e.g., tumor). Since the example methods and apparatus described herein are more sensitive than conventional systems, the reconstructed image may be more useful for diagnosing pathology. For example, smaller tumors may be visible.

Figure 4:
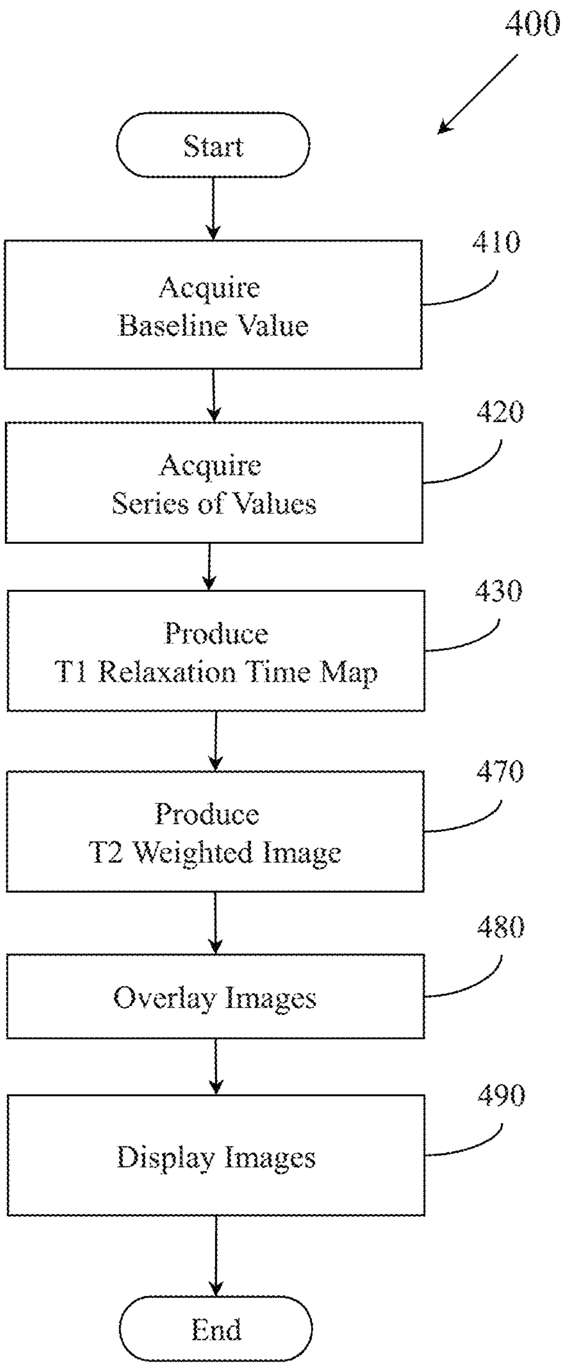
FIG. 4 illustrates a method associated with quantitative MRI using T1 mapping.

FIG. 4 illustrates a method 400. Method 400 includes some actions similar to those described in connection with method 300. For example, method 400 includes acquiring a pre-agent or baseline value at 410, acquiring a series of values at 420, and producing a T1 map at 430. However method 400 includes additional actions.

Method 400 also includes, at 470, producing a T2 weighted image. The T2 weighted image may be produced from pre-agent and post-agent NMR signals that are acquired before the change in T1 due to the contrast agent presence, while the change in T1 due to the contrast agent presence, or after the change in T1 due to the contrast agent has stopped.

Method 400 also includes, at 480, overlaying the T2 weighted image and the T1 map. Overlaying the T2 weighted image and the T1 map may include combining reconstructed images. Method 400 also includes, at 490, generating a signal or report, which may include displaying the T1 map, the T2 weighted image, or the overlay.

While method 400 illustrates acquiring a T1 relaxation time map and a T2 weighted image, other combinations of reports, images, or maps may be produced. For example, T1 weighted images, T2 weighted images, proton density images, T1 relaxation time maps, T2 relaxation time maps, or Gd concentration maps may be produced. In different embodiments, different combinations of reports, images, and maps may be overlaid to produce improved images. Since the different reports, maps, or images are built from different data sets that are acquired in different ways, the different data sets may be manipulated to produce combined data sets. For example, a resulting data set may be produced by adding data sets, by subtracting data sets, by ANDing data sets, by ORing data sets, by XORing data sets, or by other manipulations. Two or more data sets may be combined.

Figure 5:
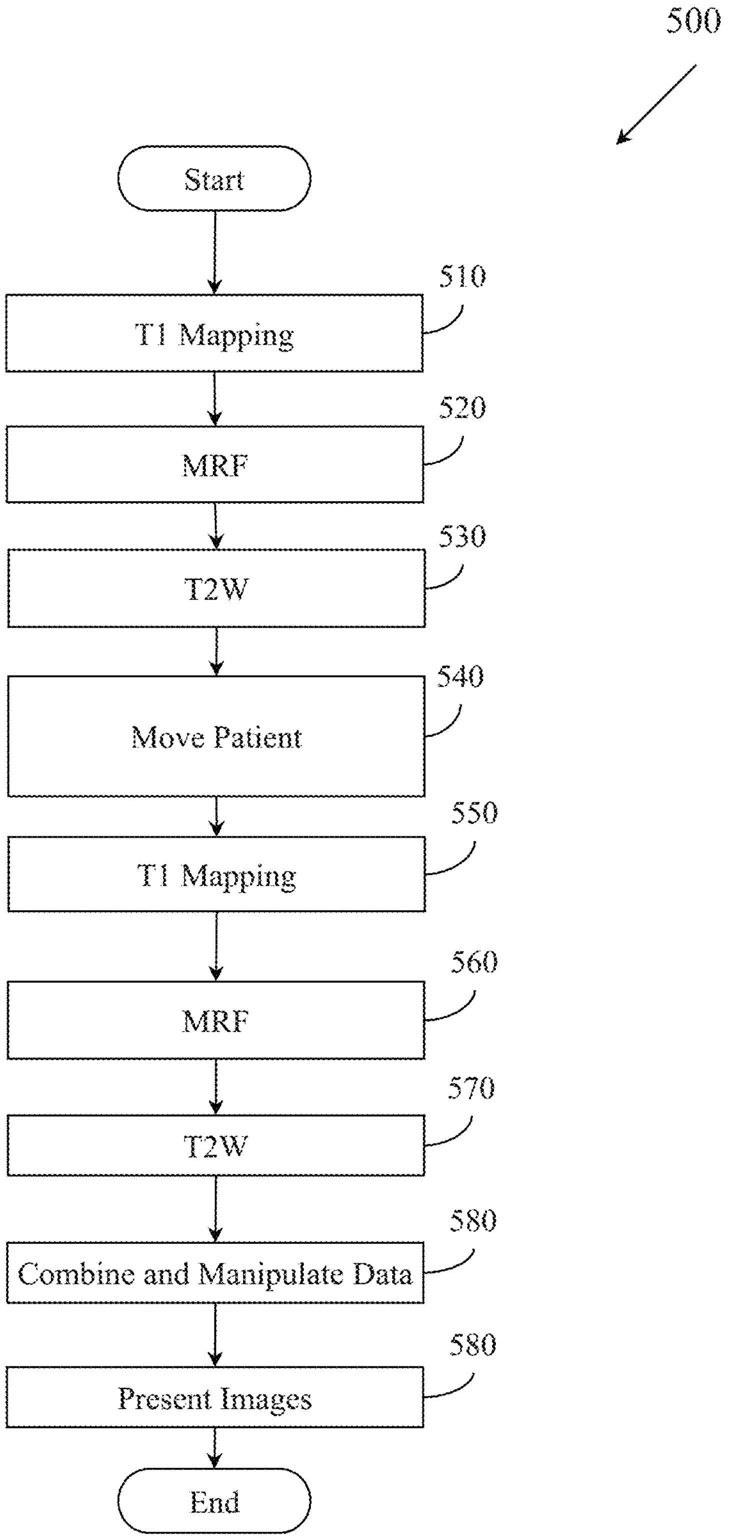
FIG. 5 illustrates a method associated with quantitative MRI using T1 mapping.

FIG. 5 illustrates a method 500. Method 500 involves performing quantitative MRI using T1 mapping in addition to other modalities to provide improved tumor detection and imaging. Method 500 includes controlling which measurements are made and when the measurements are made. Since SBK2 may be retained for up to two hours in a glioblastoma, multiple signal acquisition approaches may be employed. In one embodiment, controlling when other measurements are made may include controlling an MR apparatus to interleave different types of imaging. Since SBK2 is retained in the sample for so long, in one embodiment, an MR apparatus may be controlled to alternate between T1 signal acquisition, T2 signal acquisition, proton density signal acquisition, and combined signal acquisition via MRF to acquire different types of signal time courses. The information acquired using the different types of acquisitions may then be combined and manipulated to produce images with greater detail than is possible in single modality conventional imaging.

Method 500 includes performing T1 mapping at 510, performing MRF at 520, and performing T2 weighted imaging at 530. In different embodiments the order of steps 510, 520, and 530 may be changed. Steps 510, 520, and 530 are performed in a first MRI apparatus that operates at a first magnetic field strength (e.g., 1.5 T). Method 500 also includes, at 540, moving the patient to an MRI apparatus that operates at a second magnetic field strength (e.g., 7 T). Moving the patient may include physically relocating the patient or may include altering the operating parameters of the MRI apparatus. Once the patient has been moved, method 500 proceeds to perform T1 mapping at 550, to perform MRF at 560, and to perform T2 weighted imaging at 570. In different embodiments the order of steps 550, 560, and 570 may be changed.

With the rich and varied data acquired at steps 510, 520, 530, 550, 560, and 570 available, method 500 then proceeds, at 580, to combine and manipulate the acquired data to produce a data set(s) from which an improved image may be produced. Combining the data may include adding data together, subtracting data, providing tuples of data to a transform or other actions. In one embodiment, an image may be reconstructed from a combined data set. In another embodiment, separate images may be reconstructed and then overlaid or otherwise combined to produce an improved image. Method 500 then proceeds, at 580, to display the improved image. The improved image may allow detection of tumors smaller than a single voxel size used during signal acquisition. For example, the improved image may allow detection of tumors smaller than 1 mm in diameter.

In one embodiment, which slices or volumes are imaged, and how those slices or volumes are imaged, may depend on earlier acquired images. By way of illustration, T2 imaging or MRF may be employed to select a slice(s) or volume(s) for T1 mapping. By way of further illustration, the number or type of MRF acquisitions that are interleaved with T1 mapping acquisitions may vary inversely with the percent change in T1. Other selection criteria may be employed. Three dimensional imaging on the selected slice(s) or volume(s) may be performed. Conventionally, three dimensional imaging may not be possible due to the clearance rate of the contrast agent. Three dimensional imaging may include acquiring data in a sagittal plane, in a coronal plane, and in a transverse plane.

"Operational module", as used herein, includes but is not limited to discrete hardware, (e.g., resistors, capacitors, transistors), integrated circuits, firmware, or combinations of each to perform a function(s) or an action(s), and/or to cause a function or action from another circuit, method, and/or system. An operational module may include a software-controlled microprocessor, a discrete circuit (e.g., ASIC), an analog circuit, a digital circuit, a programmed logic device, a memory device containing instructions, and other entities. A circuit may include one or more gates, combinations of gates, or other circuit components. Where multiple operational modules are described, it may be possible to incorporate the multiple operational modules into one physical system, such as operating on a common processor or combination of hardware and software. Similarly, where a single operational module is described, it may be possible to distribute that single operational module between multiple operational modules.

Figure 6:
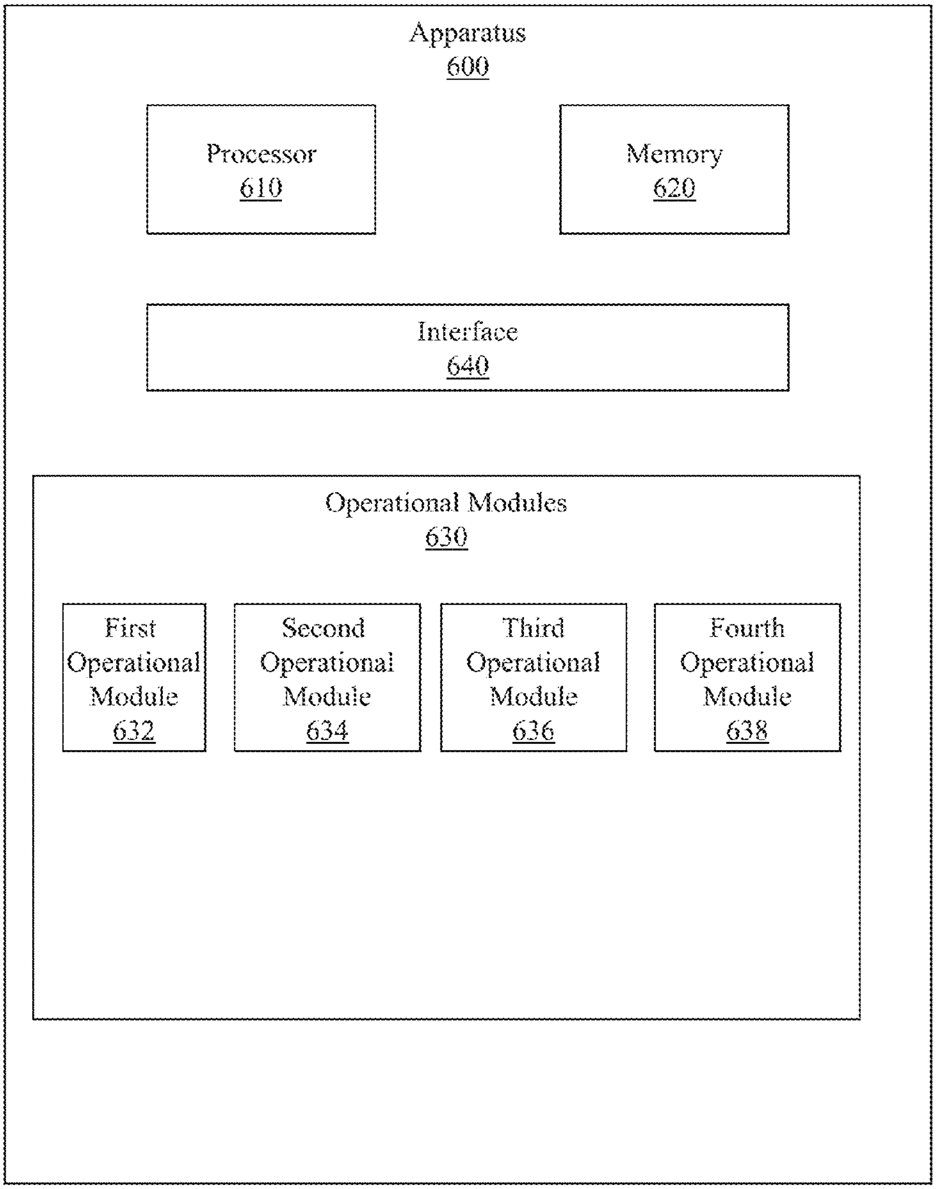
FIG. 6 illustrates an apparatus associated with quantitative MRI using T1 mapping.

FIG. 6 illustrates an apparatus 600 configured for use with an MR apparatus. Apparatus 600 includes a processor 610, a memory 620, a set of operational modules 630, and an interface 640 to connect the processor 610, the memory 620, and the set of operational modules 630. Thus, as described above, the operational modules 630 may be embodied as software stored in the memory 620 and executed by the processor 610, or may be a separate processor(s) that operates according to software stored in the memory 620 or other dedicated memory. Additionally, the operational modules 630 may include discrete hardware The set of operational modules 630 includes a first operational modules 632 that measures a baseline or pre-agent T1 in a sample when no T1 altering molecular imaging agent is present in the sample. The first operational module 632 may measure the baseline or pre-agent T1 from MR signals received from the sample after the sample was excited by an MR apparatus. For example, the first operational module 632 may measure a baseline or pre-agent T1 in a sample before a molecular imaging agent that changes T1 in a glioblastoma is presented to the sample.

The set of operational modules 630 also includes a second operational module 634 that repetitively measures T1 in the sample as affected by the presence of a molecular imaging agent in the sample. The molecular imaging agent will include a contrast agent and thus the change in T1 will be due to a change in the concentration of the contrast agent in the sample. The contrast agent may be, for example, Gadolinium, or a nanoparticle. In one example, T1 or the change in T1 may be quantified by converting the values to a concentration. In one embodiment, the second operational module 634 acquires a set of quantitative T1 measurements in the sample for a period of time exceeding thirty minutes during which the sample is experiencing a change in T1 of at least 95% of the peak change in T1 caused by the presence of the molecular imaging agent.

The set of operational modules 630 also includes a third operational module 636 that is configured to produce a T1 relaxation time map. The T1 relaxation time map illustrates changes in T1 in the sample over time.

The set of operational modules 630 also includes a fourth operational module 638 that is configured to generate a signal identifying whether a target material is present in the sample. In one embodiment, fourth operational module 638 identifies whether the target material is present as a function of the baseline or pre-agent T1, the change in T1 due to the molecular imaging agent, or the T1 relaxation time map. For example, when the peak concentration of Gd exceeds a threshold amount and remains within a pre-determined percentage of that peak concentration, then the sample is identified as including the material. In one embodiment, the fourth operational module 638 generates a signal upon identifying that a glioblastoma is present in the sample, where the identifying is performed as a function of the baseline or pre-agent T1 and the set of T1 measurements. In one embodiment, when the molecular imaging agent is SBK2, the characterization of a region as being a glioblastoma may be made when the concentration of Gd reaches at least 0.08 mM and remains above 0.07 mM for at least 30 minutes. In another embodiment, similar quantitative measurements would be made to distinguish other tumor types.

In one embodiment, the specific molecular imaging agent is SBK2 conjugated to Tris-$(Gd\text{-}DOTA)_3$. In another embodiment, the specific molecular imaging agent is SBK2 conjugated to Lys-DOTA that is a single Gd chelate. Other specific molecular imaging agents may have different peptides or polypeptides conjugated to different contrast agents (e.g., magnetic nanoparticles).

Apparatus 600 is much more sensitive than conventional apparatus. In one embodiment, the fourth operational module 638 is configured to generate the signal or report upon determining that the target material occupies less than 50% of the voxel, less than 25% of the voxel, less than 10% of the voxel, less than 1% of the voxel, or under other conditions. In other embodiments, the fourth operational module 638 may be configured to generate the signal or report upon determining a change in concentration of the contrast agent of at least 1000 nM, of at least 500 nM, or of at least 250 nM. Other changes in concentrations may be employed in other examples. The signal or report may include, for example, a visual signal, an audible signal, an electrical signal, a computer interrupt, a procedure call, a voltage on a line, a frequency on a line, or other signal.

Processor 610 may be, for example, a signal processor, a microprocessor, an application specific integrated circuit (ASIC), or other control and processing circuitry for performing tasks including signal coding, data processing, input/output processing, power control, or other functions. Memory 620 can include non-removable memory or removable memory. Non-removable memory may include random access memory (RAM), read only memory (ROM), flash memory, a hard disk, or other memory storage technologies. Removable memory may include flash memory, or other memory storage technologies, such as "smart cards." Memory 620 may be configured to store the baseline or pre-agent value, the non-specific uptake value, the specific uptake value, or other information.

In one embodiment, the apparatus 600 may be a general purpose computer that has been transformed into a special purpose computer through the inclusion of the set of operational modules 630. The term "computer" as used herein may refer to traditional computer system, including desktops and laptops, or may include mobile computing devices, such as phones, tablets, and the like. Furthermore, "computer" as used herein may refer to specialized systems that include hardware, such as processors and memory, and specialized hardware or software, such as wearable computing devices and the like. Again, the operational modules 630 may be dedicated circuits, processors, or computers that carry out specific functions, or may be reflected as instruction sets that are carried out by the processor 610 to complete the functions. The set of operational modules 630 may be configured to perform input and output. Apparatus 600 may interact with other apparatus, processes, and services through, for example, a computer network. Elements of the apparatus 600 may be configured to communicate with each other, but not all connections have been shown for clarity of illustration.

Figure 7:
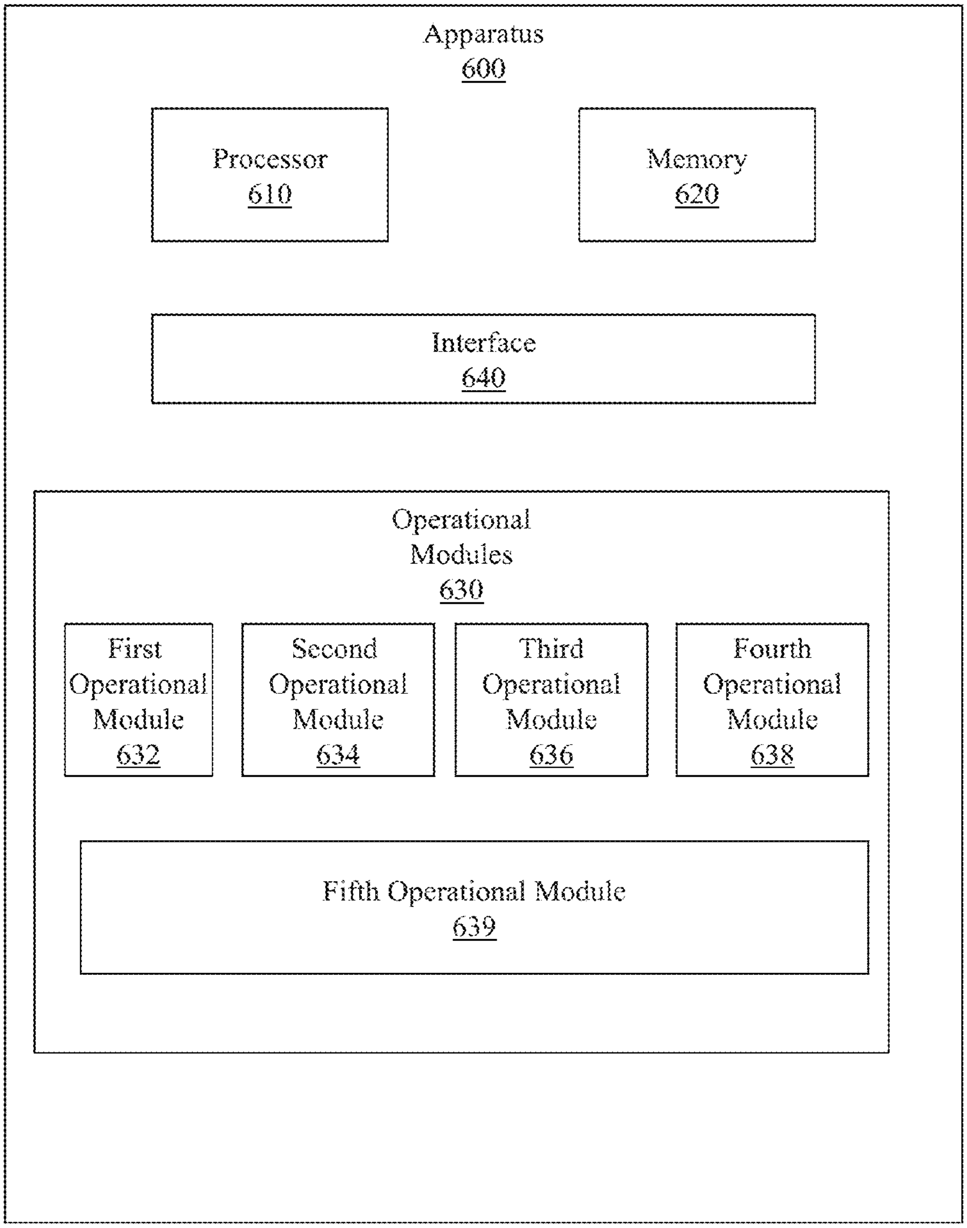
FIG. 7 illustrates an apparatus associated with quantitative MRI using T1 mapping.

FIG. 7 illustrates another embodiment of apparatus 600 (FIG. 6). This embodiment of apparatus 600 includes a fifth operational module 639 that is configured to control the timing and type of measurements that are taken. Controlling the order in which measurements are taken facilitates acquiring richer signal sets. The fifth operational module 639 may determine a time for measuring the baseline or pre-agent T1. The time may include a start time, an end time, a duration, or other information for controlling when the baseline or pre-agent T1 will be measured. Since T1 values are not quantitative by themselves, acquiring the baseline or pre-agent value facilitates quantifying relative values. The fifth operational module 639 may also determine start and end times for performing signal acquisition for T1 mapping, T1 imaging, T2 mapping, T2 imaging, proton density imaging, and MRF. The start and end times may be determined by a time at which a peak change in T1 is detected and by a time during which the change in T1 stays within a threshold amount of the peak change. For example, signal acquisition for T1 mapping may start after the T1 peak change is detected and continue for thirty minutes thereafter. MRF acquisitions may be interleaved periodically (e.g., every five minutes) with the other acquisition. The fifth operational module 639 may manipulate data acquired for the different types of NMR acquisitions. In different embodiments manipulating the data may include adding data, subtracting data, ANDing data, ORing data, XORing data, binning data, or other operations. The fifth operational module 639 may then produce an image from the combined and manipulated data. For example, the fifth operational module 639 may subtract baseline or pre-agent T1 data from T1 data acquired later, produce an image from the resulting data, and overlay that image on a T2 weighted image. In another embodiment, the fifth operational module 639 may produce a combined image that is an overlay of the points in various images that all indicate the presence of a contrast agent. All other data points may be removed to leave only an image of a tumor. The tumor may then be overlaid on, for example, a high resolution image of non-tumor anatomy.

In one embodiment, NMR signal data may be acquired in a coronal plane, in a sagittal plane, and in a transverse plane. When this type of data is acquired, then a three dimensional image of the tumor may be reconstructed and presented. Conventionally, it may have been difficult, if even possible at all, to acquire contrast enhanced three dimensional images of tumors due to the short time during which contrast agents were present, particularly for small tumors.

The type of imaging described above is only possible when the specific imaging agent (e.g., SBK2) is retained in the tumor long enough to allow the multiple types of imaging. FIGS. 1, 12-17, and 25-27 show that SBK2 has adequate retention time to support this type of complex imaging.

Figure 8:
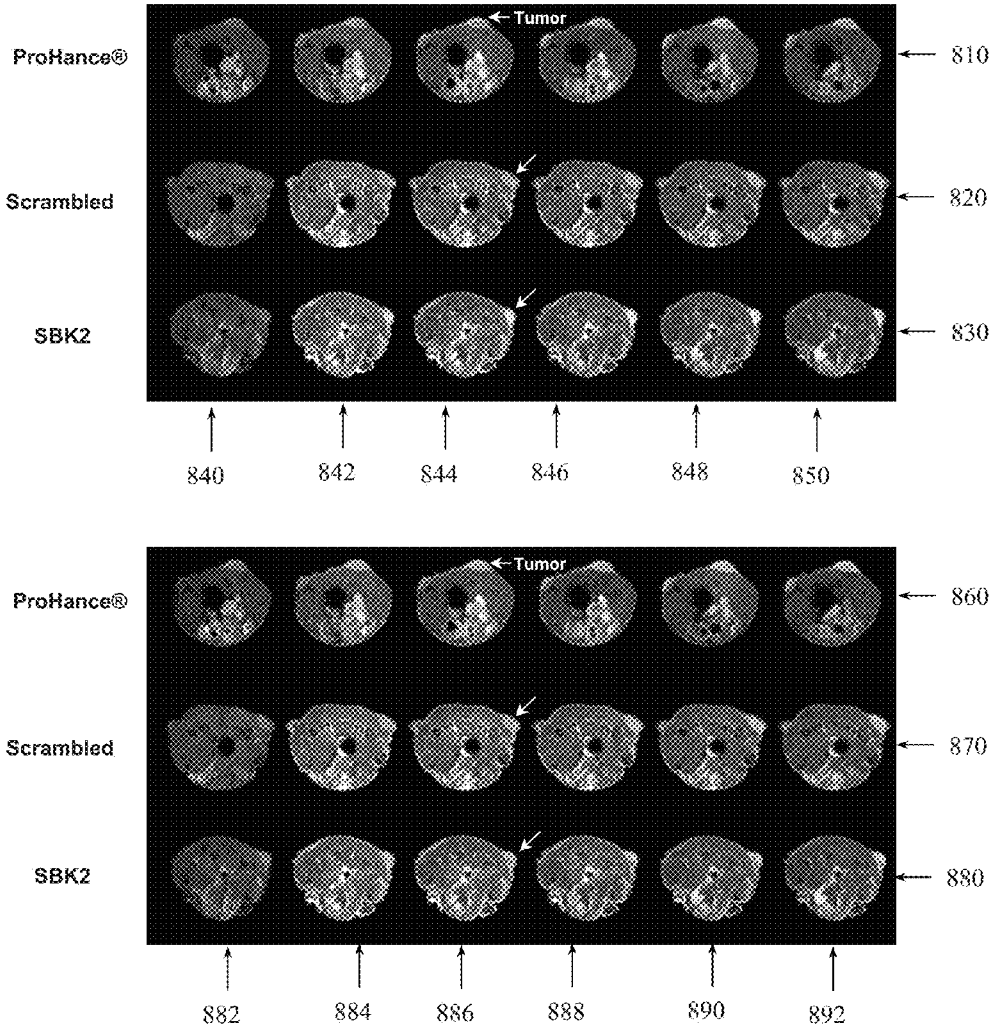
FIG. 8 illustrates that the SBK2 targeted contrast agent improves the enhancement of LN-229 tumors.

FIG. 8 illustrates that the SBK2 based specific molecular imaging agent improves the enhancement of LN-229 tumors. FIG. 8 illustrates representative T1-weighted axial 2D gradient images of LN-229 flank tumor-bearing mice before (pre-injection) (column 840) and at 1 minute (column 842), 5 minutes (column 844), 10 minutes (column 846), 20 minutes (column 848), and 30 minutes (column 850) after the intravenous injection of ProHance™ (row 810), scrambled Tris-(Gd-DOTA)$_3$ (row 820), or SBK2-Tris-(Gd-DOTA)$_3$ (row 830) at 0.1 mmol Gd/kg. FIG. 8 also illustrates axial 2D gradient images heat map overlays on the tumor to indicate contrast intensity. FIG. 8 illustrates heat maps with overlays for T1-weighted axial 2D gradient images of LN-229 flank tumor-bearing mice before (pre-injection) (column 882) and at 1 minute (column 884), 5 minutes (column 886), 10 minutes (column 888), 20 minutes (column 890), and 30 minutes (column 892) after the intravenous injection of ProHance™ (row 860), scrambled Tris-(Gd-DOTA)$_3$ (row 870), or SBK2-Tris-(Gd-DOTA)$_3$ (row 880) at 0.1 mmol Gd/kg.

While FIG. 8 demonstrates improved contrast, these conventional T1-weighted imaging techniques still rely on relative signal intensity changes over time and are inherently qualitative at each time point. The T1-weighted values of a given region of interest are relative to the values from another area. In contrast to T1-weighted imaging, T1 relaxation time mapping is a quantitative approach that allows measurement of T1 values. When acquired dynamically, the T1 relaxation time values facilitate objectively, quantitatively, and longitudinally comparing the change in T1 at different time points. Since T1 relaxation values depend on contrast agent concentration, T1 mapping facilitates quantitatively determining contrast agent concentration in tumors. The quantitative value for contrast agent concentration or change in contrast agent concentration may then be used to characterize a tissue. For example, if the concentration is above a threshold (e.g., 50%, 0.08 mM) then the tissue may be identified as being tumor tissue.

The SBK2 based specific molecular imaging agent was developed as a diagnostic imaging tool. To function as an imaging tool, SBK2 was conjugated to a Gd chelate [SBK2-Tris-(Gd-DOTA)$_3$] to generate an MR-detectable molecular imaging agent. The ability of SBK2-Tris-(Gd-DOTA)$_3$ to function as a contrast agent was compared to a macrocyclic gadolinium chelate (Gadoteridol, ProHance™) and to a scrambled molecular imaging agent linked to gadolinium [scrambled Tris-(Gd-DOTA)$_3$]. SBK2-Tris-(Gd-DOTA)$_3$ labeled human glioma tumors with a high level of contrast persisting for two hours. The contrast enhancement of SBK2-Tris-(Gd-DOTA)$_3$ was significantly higher than that observed with ProHance™ alone. SBK2-Tris-(Gd-DOTA)$_3$ labeling of PTPμ extracellular fragment retained in the tumor microenvironment is a more specific MR molecular imaging agent than a nonspecific gadolinium chelate.

The SBK2 peptide was conjugated to Gd-DOTA using an increased molar ratio of Gd-DOTA monoamide to peptide to generate an MR-visible molecular imaging agent [SBK2-Tris-(Gd-DOTA)$_3$]. A scrambled version of the SBK2 peptide was also conjugated to Gd-DOTA to generate a non-targeted control agent [scrambled Tris-(Gd-DOTA)$_3$]. The SBK2 peptide with an N-terminal cysteine (C-GEGDDFN-WEQVNTLTKPTSD) SEQ ID NO: 1 was synthesized using standard solid-phase peptide synthesis. Matrix-assisted laser desorption/ionization time-of-flight (MALDI-TOF; Autoflex Speed, Bruker) mass spectra (m/z, $M^+$) were given as follows: 2355.52 (observed) and 2355.00 (calculated). Scrambled peptide (C-GFTQPETGTDNDLWSVDNEK) SEQ ID NO: 2 was synthesized by the same method [MALDI-TOF (m/z, $M^+$): 2355.56 (observed); 2355.00 (calculated)]. SBK2 was conjugated to maleimido-Tris-propargyl, then subsequently to azido-(Gd-DOTA). The reaction was traced by MALDI-TOF until Gd-DOTA was fully attached [MALDI-TOF (m/z, $M^+$): 4664.87 (observed); 4664.62 (calculated); Inductively coupled plasma optical emission spectroscopy (ICP-OES) analysis for $Gd^{3+}$ content: 9.56% (observed); 10.1% (calculated)]. Scrambled Tris-(Gd-DOTA)$_3$ was synthesized by the same method with a yield of 68% [MALDI-TOF (m/z, M+): 4664.75 (observed); 4664.62 (calculated); ICP ($Gd^{3+}$ content): 9.68% (observed); 10.1% (calculated)].

Figure 9:
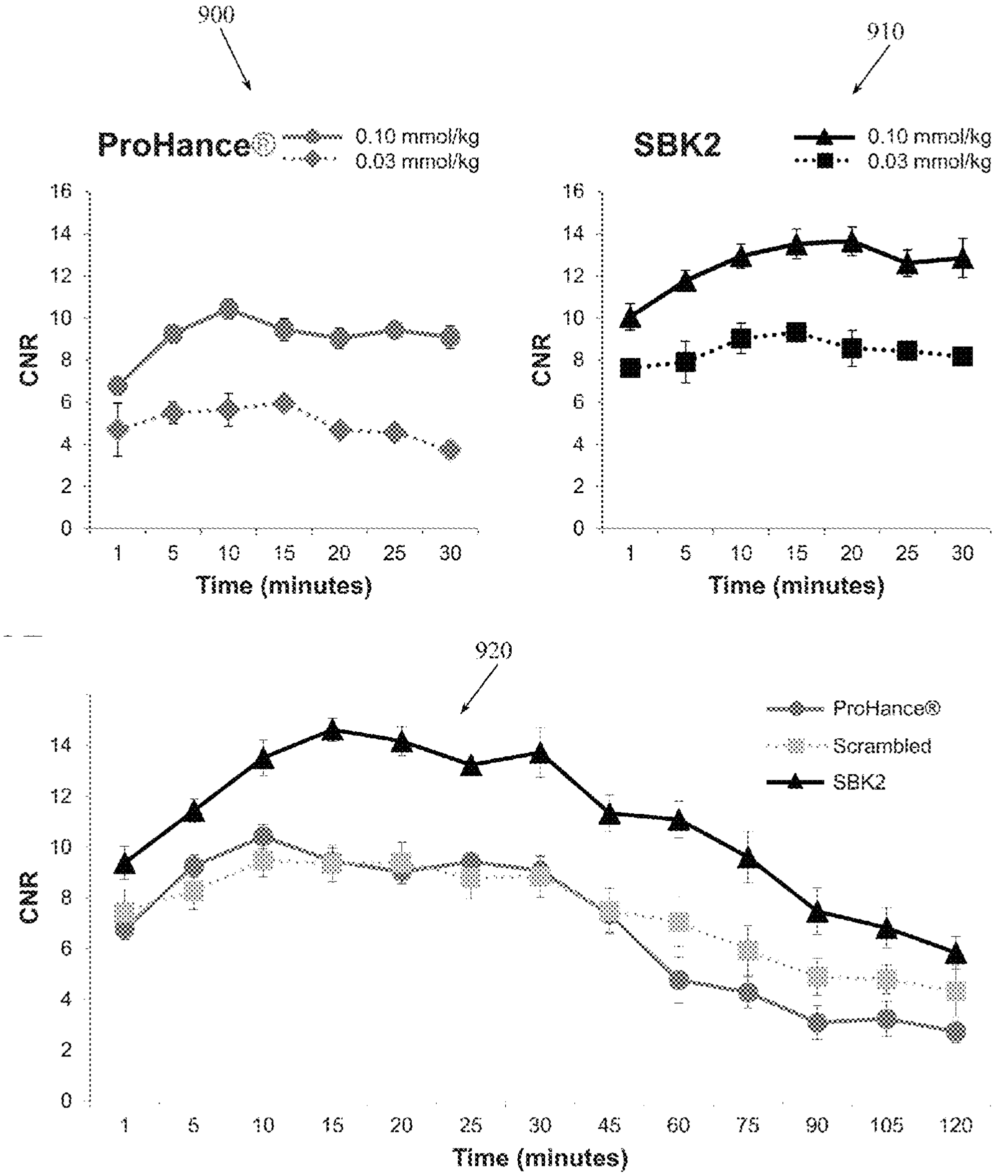
FIG. 9 illustrates quantitation of LN-229 flank tumor enhancement following administration of control or targeted contrast agents and illustrates a comparison of LN-229 flank tumor contrast to noise ratio (CNR) over a 2-hour period following intravenous administration of ProHance™, scrambled Tris-(Gd-DOTA)$_3$, or SBK2-Tris-(Gd-DOTA)$_3$ contrast agents.

FIG. 9 illustrates quantitation of LN-229 flank tumor enhancement following administration of control or targeted contrast agents in xenograft mice. Graphs 900 and 910 illustrate dose-response plots of LN-229 flank tumor contrast to noise ratio (CNR) with ProHance™ or SBK2-Tris-(Gd-DOTA)$_3$ respectively administered at 0.03 mmol Gd/kg or 0.1 mmol Gd/kg.

Graph 920 illustrates a comparison of LN-229 flank tumor CNR over a 2-hour period following intravenous administration of ProHance™, scrambled Tris-(Gd-DOTA)$_3$, or SBK2-Tris-(Gd-DOTA)$_3$ contrast agents (0.1 mmol Gd/kg). Data is shown as means±SEM. The targeted agent SBK2-Tris-(Gd-DOTA)$_3$ showed improved tumor CNR when compared with the nontargeted scrambled Tris-(Gd-DOTA)$_3$ or ProHance™. SBK2-Tris-(Gd-DOTA)$_3$ resulted in an approximate 55% increase in tumor CNR over scrambled Tris-(Gd-DOTA)$_3$ or ProHance™ at 15 to 45 minutes post-injection ($P<0.001$). At 60 to 120 minutes post-injection, the ProHance™ cleared more rapidly than SBK2-Tris-(Gd-DOTA)$_3$ resulting in greater than 110% increase in SBK2-Tris-(Gd-DOTA)$_3$ tumor CNR compared with ProHance™ ($P<0.001$). The SBK2-Tris-(Gd-DOTA)$_3$ tumor CNR was approximately 53% greater than the scrambled Tris-(Gd-DOTA)$_3$ tumor CNR at 60 to 90 minutes ($P<0.001$).

Figure 10:
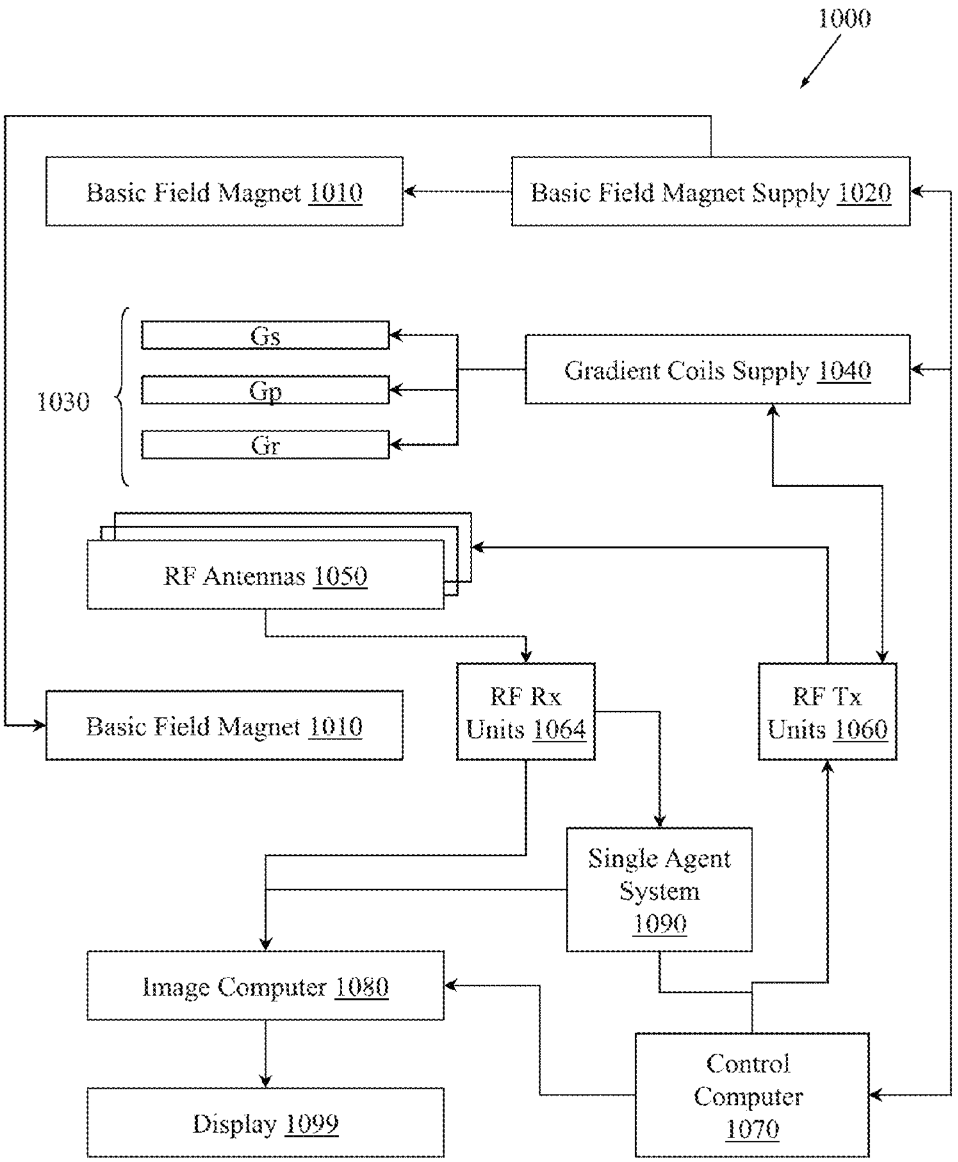
FIG. 10 illustrates an MRI apparatus configured to perform quantitative MRI using T1 mapping.

FIG. 10 illustrates an example MRI apparatus 1000 configured with a single agent system 1090. The apparatus 1000 includes a basic field magnet(s) 1010 and a basic field magnet supply 1020. Ideally, the basic field magnets 1010 would produce a uniform B0 field. However, in practice, the B0 field may not be uniform, and may vary over an object being imaged by the MRI apparatus 1000. MRI apparatus 1000 may include gradient coils 1030 configured to emit gradient magnetic fields like Gs, GP and GR. The gradient coils 1030 may be controlled, at least in part, by a gradient coils supply 1040. In some examples, the timing, strength, and orientation of the gradient magnetic fields may be controlled, and thus selectively adapted, during an MRI procedure.

MRI apparatus 1000 may include a set of RF antennas 1050 that are configured to generate RF pulses and to receive resulting MR signals from an object to which the RF pulses are directed. In some examples, how the pulses are generated and how the resulting MR signals are received may be controlled, and thus may be selectively adapted, during an MRI procedure. Separate RF transmission and reception-coils can be employed. The RF antennas 1050 may be controlled, at least in part, by a set of RF transmission units 1060.

The gradient coils supply 1040 and the RF transmission units 1060 may be controlled, at least in part, by a control computer 1070. In one example, the control computer 1070 may be programmed to perform methods like those described herein. The MR signals received from the RF antennas 1050 can be employed to generate an image, and thus may be subject to a transformation process like a two dimensional FFT that generates pixilated image data. The transformation can be performed by an image computer 1080 or other similar processing device. The image data may then be shown on a display 1099. While FIG. 10 illustrates an example MRI apparatus 1000 that includes various components connected in various ways, it is to be appreciated that other MRI apparatus, NMR apparatus, or MR apparatus may include other components connected in other ways.

Single agent system 1090 may operate as a controlling apparatus 1000 to use a quantitative relaxometry approach like those described herein. Single agent system 1090 may also provide means for providing a signal as a function of the effect of a molecular imaging agent on T1 in the sample. The signal may be, for example, a visual signal, an audible signal, an electrical signal, a computer interrupt, a procedure call, a voltage on a line, a frequency on a line, or other signal.

Figure 11:
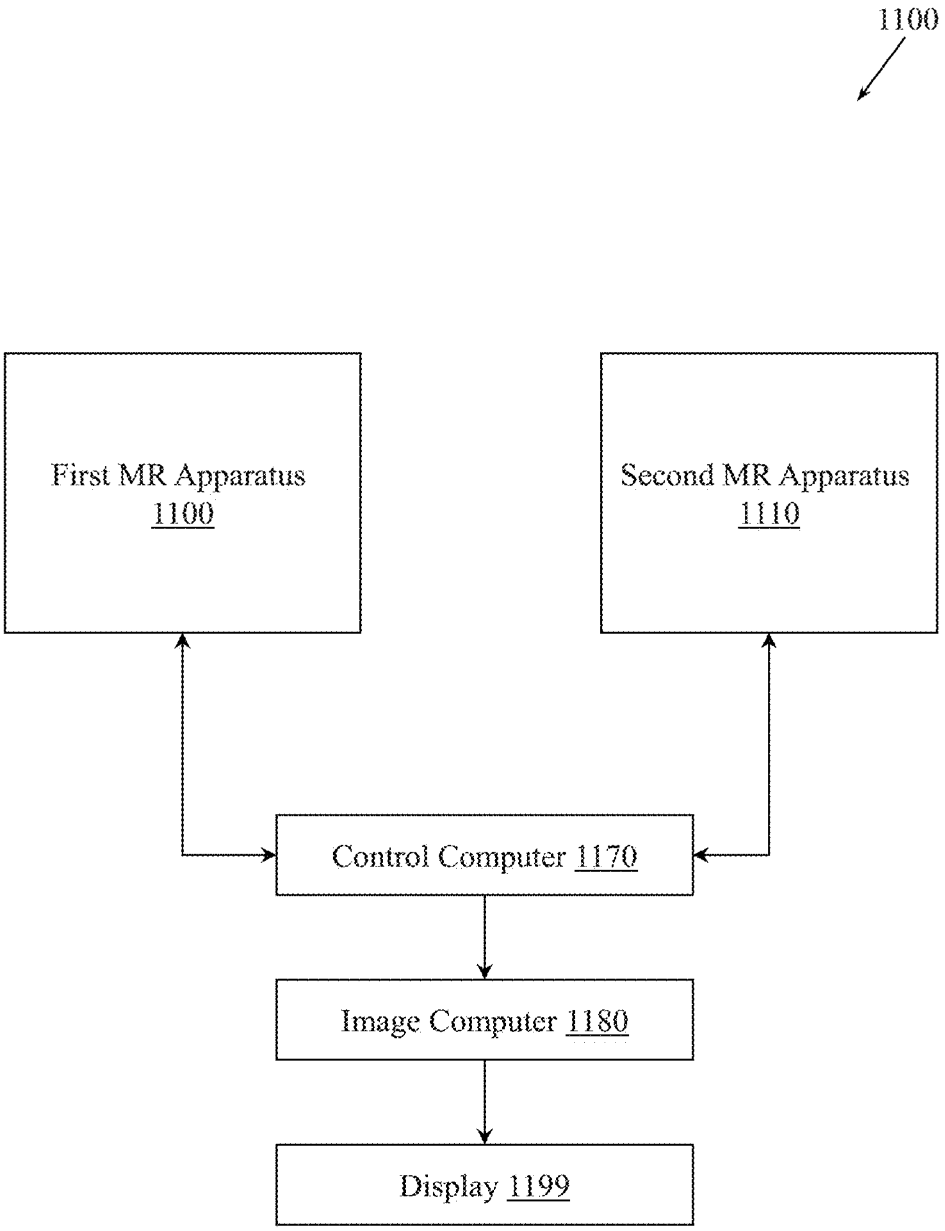
FIG. 11 illustrates an MRI apparatus configured to perform quantitative MRI using T1 mapping.

FIG. 10 illustrates an apparatus 1000 that operates with a single main magnetic field strength. Apparatus with different main magnetic field strengths have different impacts on spatial resolution and content agent intensity. Therefore, FIG. 11 illustrates an apparatus configured to perform MRI using two different main magnetic field strengths. A first MRI apparatus 1100 may operate at a first main field strength (e.g., 1.5 T). A second MRI apparatus 1110 may operate at a second main field strength (e.g., 7 T). A control computer 1170 may be configured to control imaging in the two different apparatus. An image computer 1180 may then produce an image from data acquired from the two different apparatus and display the image on display 1199. Since SBK2 is retained for up to two hours, a patient may be imaged in first apparatus 1100 for a period of time and then be moved and imaged in the second apparatus 1110 for a second period of time. This may facilitate resolving the dilemma concerning trading contrast for spatial resolution. Images acquired in the higher field system may provide superior spatial resolution and images acquired in the lower field system may provide superior contrast. An overlay of the two images may provide a superior image than can be acquired in any single machine.

Figure 12:
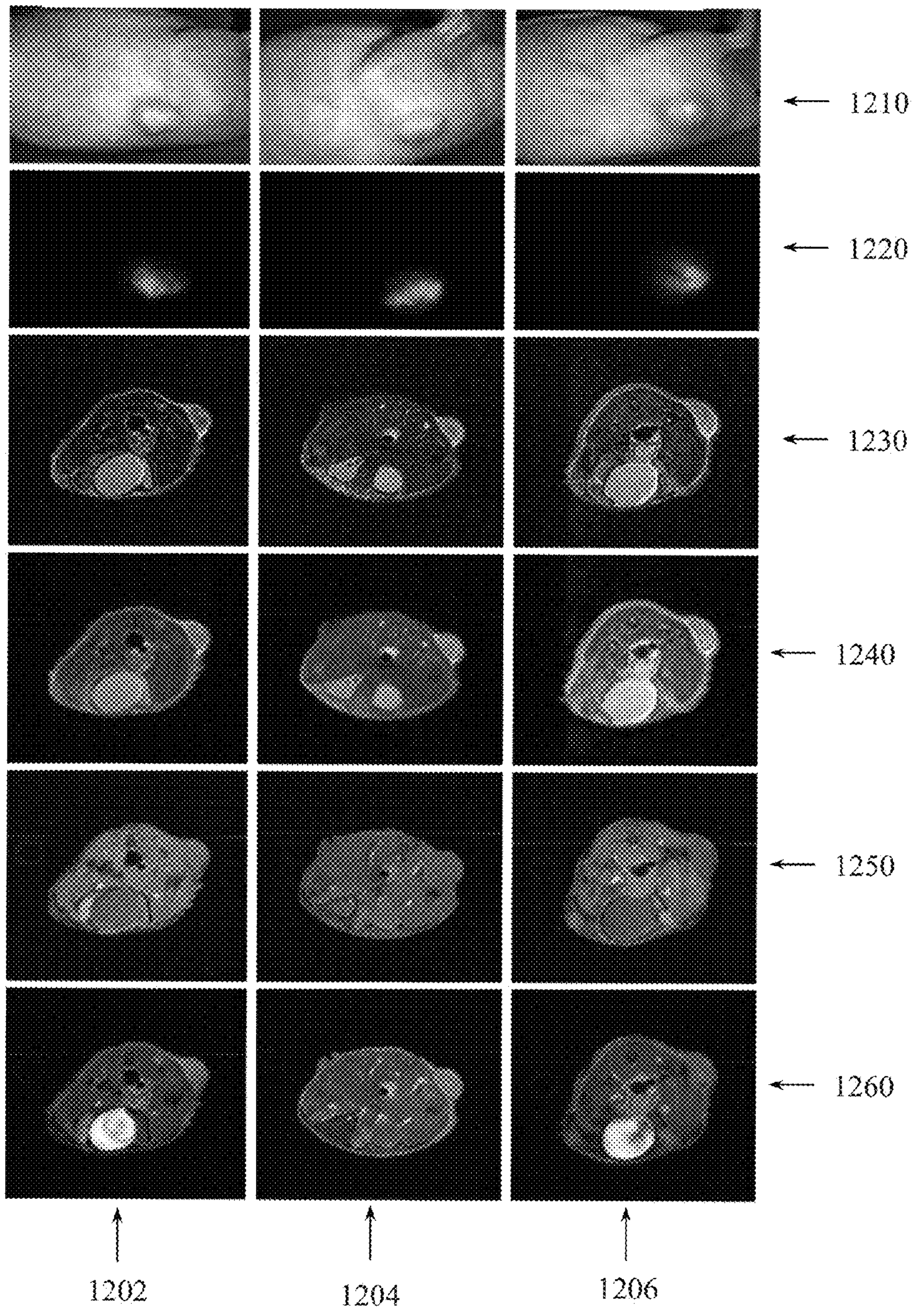
FIG. 12 illustrates how specific and non-specific molecular imaging agents enhance LN-299 tumors.

FIG. 12 illustrates how the SBK2-Tris-(Gd-DOTA)$_3$ molecular imaging agent and the non-specific agents all enhance LN-229 tumors. Representative bright-field images of GFP-positive LN-229 flank tumors for animals where 0.2 mmol Gd/kg of Optimark™, scrambled-Tris-(Gd-DOTA)$_3$, or SBK2-Tris-(Gd-DOTA)$_3$ was administered are presented in row 1210 in columns 1202, 1204, and 1206 respectively. GFP fluorescence images of LN-229 tumor cells for each of the three contrast agents are presented in row 1220 in columns 1202, 1204, and 1206 respectively. T2 high resolution images are presented in row 1230 in columns 1202, 1204, and 1206 respectively. T2 low-resolution images with a region of interest (ROI) illustrated by a dashed line are presented in row 1240 in columns 1202, 1204, and 1206 respectively show the tumor area used for T1 map quantification. Axial T1-weighted images of LN-229 flank tumor at baseline or pre-agent (e.g., before injection of contrast agents) are shown in row 1250. Axial T1-weighted images of LN-229 flank tumor at time of maximum contrast (e.g., 15 minutes) following intravenous injection are shown in row 1260.

High-resolution T2-weighted images were obtained for each mouse using a RARE (Rapid Acquisition with Relaxation Enhancement) acquisition (TR/TE=5000/40 ms, 20 slices, resolution=0.117×0.117×0.5 mm) to select the imaging slice for the dynamic T1 mapping acquisition. The dynamic T1 data were then acquired using a snapshot GRE (Gradient Recalled Echo) acquisition with inversion recovery preparation (10 inversion times [263, 775, 1287, 1799, 2311, 2823, 3335, 3847, 4359, and 4871 ms], GRE imaging readout TR/TE=4.0 ms/1.3 ms, flip angle=10 degrees, resolution=0.234×0.234×1 mm, Field of View (FOV)=30×30 mm, and 10 signal averages). The total acquisition time for each T1 mapping scan was 2.5 min. After five baseline/pre-agent T1 mapping scans, Optimark™, the targeted SBK2-Tris-(Gd-DOTA)$_3$ agent, or the non-targeted scrambled-Tris-(Gd-DOTA)$_3$ control was injected at a dose of 0.2 mmol of Gd/kg followed by a 50 μL flush of saline. T1 maps were then consecutively acquired every 2.5 min over 62.5 min.

The MRI data were imported into MATLAB enabling estimation of both pixel-wise T1 relaxation time maps as well as mean intra-tumoral T1 changes using an ROI analysis. The T1 maps were obtained from the T1 mapping acquisition mono-exponential models. To compare the multiple imaging agents, the pre and post-agent T1 maps were then used to calculate maps of percent change in T1, which is directly related to the concentration of each agent within the tumor. To calculate Gd concentrations, T1 relaxivity constants determined at 9.4 T were used along with T1 map values.

As the T1 maps and T2-weighted images were co-registered, the ROI analysis was performed by outlining the ROI on the T2-weighted images. The same ROI was then applied to all of the T1 maps and the average value in the ROI was calculated as a measure of tumor uptake of each imaging agent. Plots of normalized T1 values in the tumor were calculated by dividing the post-agent injection T1 maps by an average of the 5 baseline (pre-agent injection) tumor T1 values. This normalization was performed to limit the effects of variation in the pre-contrast tumor T1 values on the comparison of the molecular imaging agents.

As an imaging marker for contrast agent retention, a slope analysis was performed on the normalized T1 values. Slopes were calculated for Optimark™, scrambled-Tris-(Gd-DOTA)$_3$, and SBK2-Tris-(Gd-DOTA)$_3$ by using all of the mean tumor T1 values from 15 minutes to 60 minutes following agent administration. For each pair of contrast agents, normalized T1 map values at each time point, along with the slopes of post-agent T1 curves were evaluated for statistical significance using a two-tailed Student's t-test, assuming statistical significance at $p<0.05$. An F-test was also used to determine if the variance was significantly different between the two samples being compared.

Figure 13:
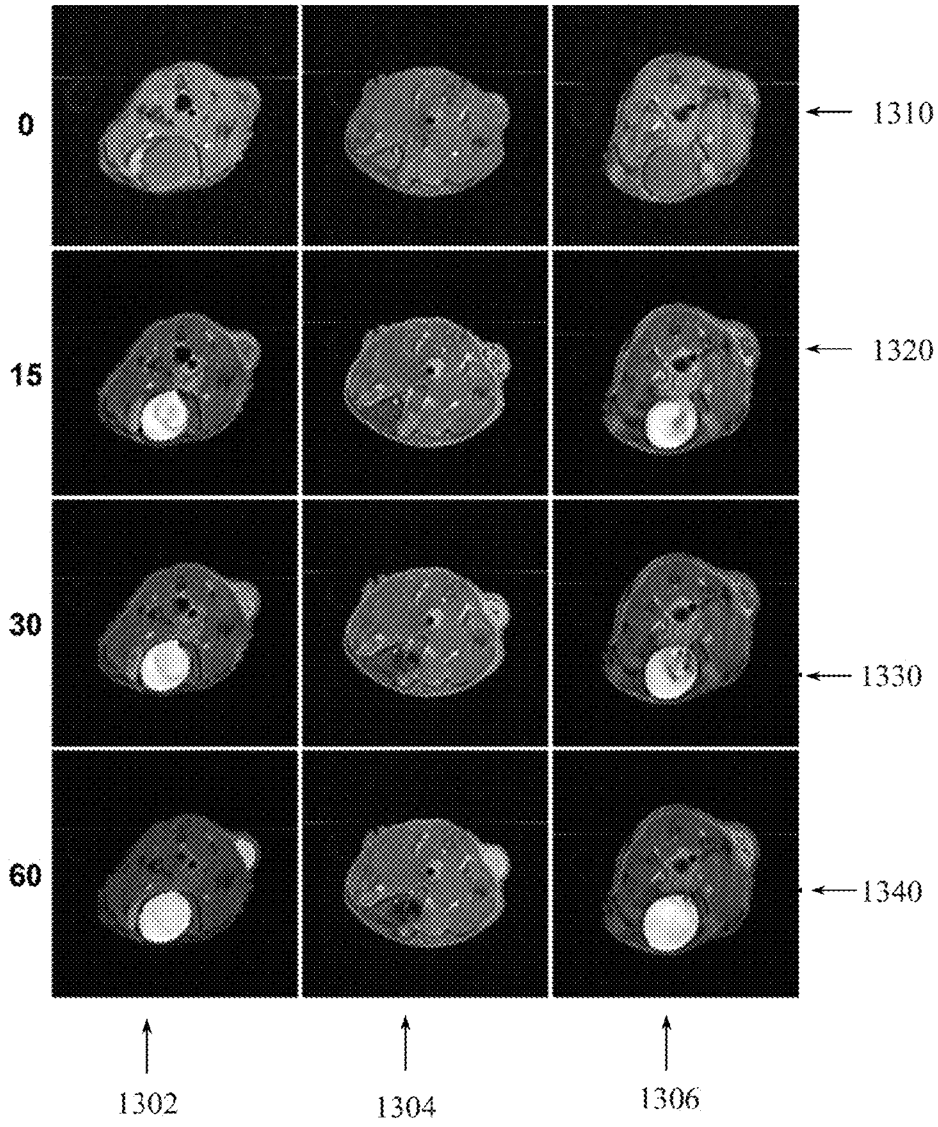
FIG. 13 illustrates a quantitative comparison of the difference in tumor enhancement over time between three different molecular imaging agents.

FIG. 13 illustrates a quantitative comparison of the difference in tumor enhancement over time between the three contrast agents. Row 1302 illustrates images associated with the Optimark™ agent. Row 1304 illustrates images associated with the scrambled agent. Row 1306 illustrates images associated with the SBK2 agent. T1 mapping was employed to compare the changes in T1 relaxation times in the tumor for the contrast agents over time. Pixel-wise maps of T1 relaxation time were normalized to the mean baseline or pre-agent T1 values and are shown as heat maps overlaying the corresponding gray scale axial images for the indicated time points. All of the contrast agents produced a reduction in T1 relaxation time within the first 15 minutes after agent injection.

The specific molecular imaging agent SBK2-Tris-(Gd-DOTA)$_3$ results in prolonged decrease in T1 relaxation time in tumors compared to non-specific agents. Normalized T1 maps of the flank tumors overlaid onto T1-weighted images are presented at pre-contrast (0 minutes)(row 1310); 15 minutes post-injection (row 1320); 30 minutes post-injection (row 1330); and 60 minutes post-injection (row 1340). Note the prolonged decrease in normalized T1 values with the SBK2-Tris-(Gd-DOTA)$_3$ agent resulting in lower T1 map values while the T1 values of the non-specific agents have returned to about 60% of baseline or pre-agent.

Figure 14:
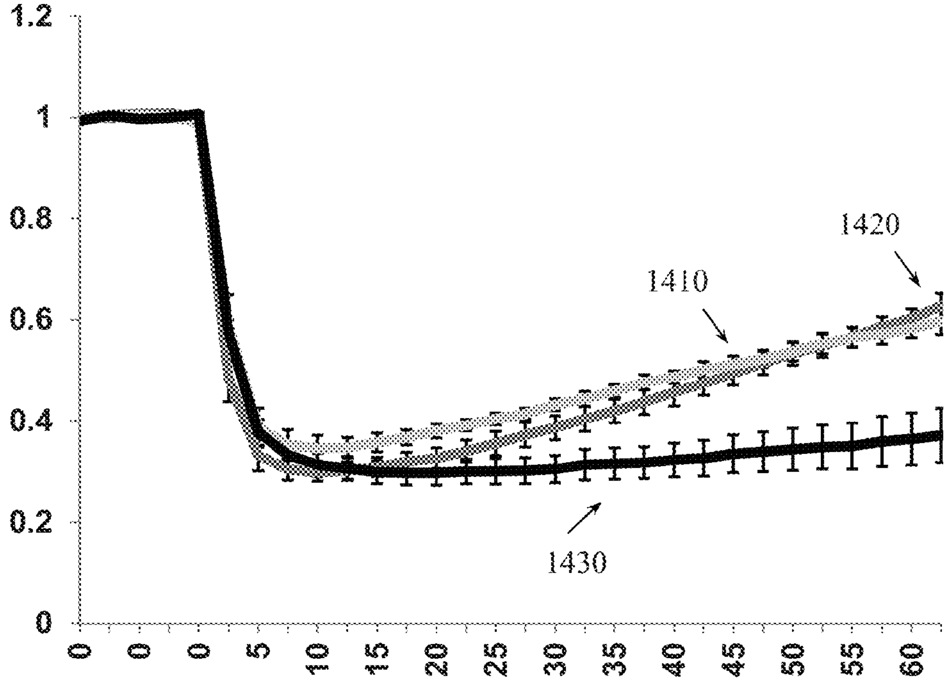
FIG. 14 illustrates mean tumor normalized T1 values over time following administration of contrast agents.

FIG. 14 illustrates mean tumor normalized T1 values following intravenous administration of Optimark™, scrambled-Tris-(Gd-DOTA)$_3$, or SBK2-Tris-(Gd-DOTA)$_3$ contrast agents in cohorts of nu/nu athymic mice bearing glioma flank tumors administered at a dose of 0.2 mmol Gd/kg. The slope for SBK2 is illustrated in line 1430. The slopes for Optimark™ and scrambled are illustrated in lines 1410 and 1420 respectively. Note the sustained decrease in normalized T1 for SBK2-Tris-(Gd-DOTA)$_3$ as well as the significant difference in slope due to agent clearance between the non-specific agents compared to SBK2-Tris-(Gd-DOTA)$_3$, which showed the highest retention. FIG. 14 illustrates mean tumor normalized T1 values at baseline or pre-agent and after agent injection measured every 2.5 minutes for 62.5 minutes. Normalized T1 values are significantly different between SBK2-Tris-(Gd-DOTA)$_3$ and Optimark™ from 30-62.5 minutes (ranges from $p<0.001$ to $p<0.04$ depending upon the time point), and between SBK2-Tris-(Gd-DOTA)$_3$ and scrambled-Tris-(Gd-DOTA)$_3$ from 17.5-62.5 minutes (ranges from $p<0.002$ to $p<0.03$). Optimark™ and scrambled-Tris-(Gd-DOTA)$_3$ were not significantly different at any time point.

Figure 15:
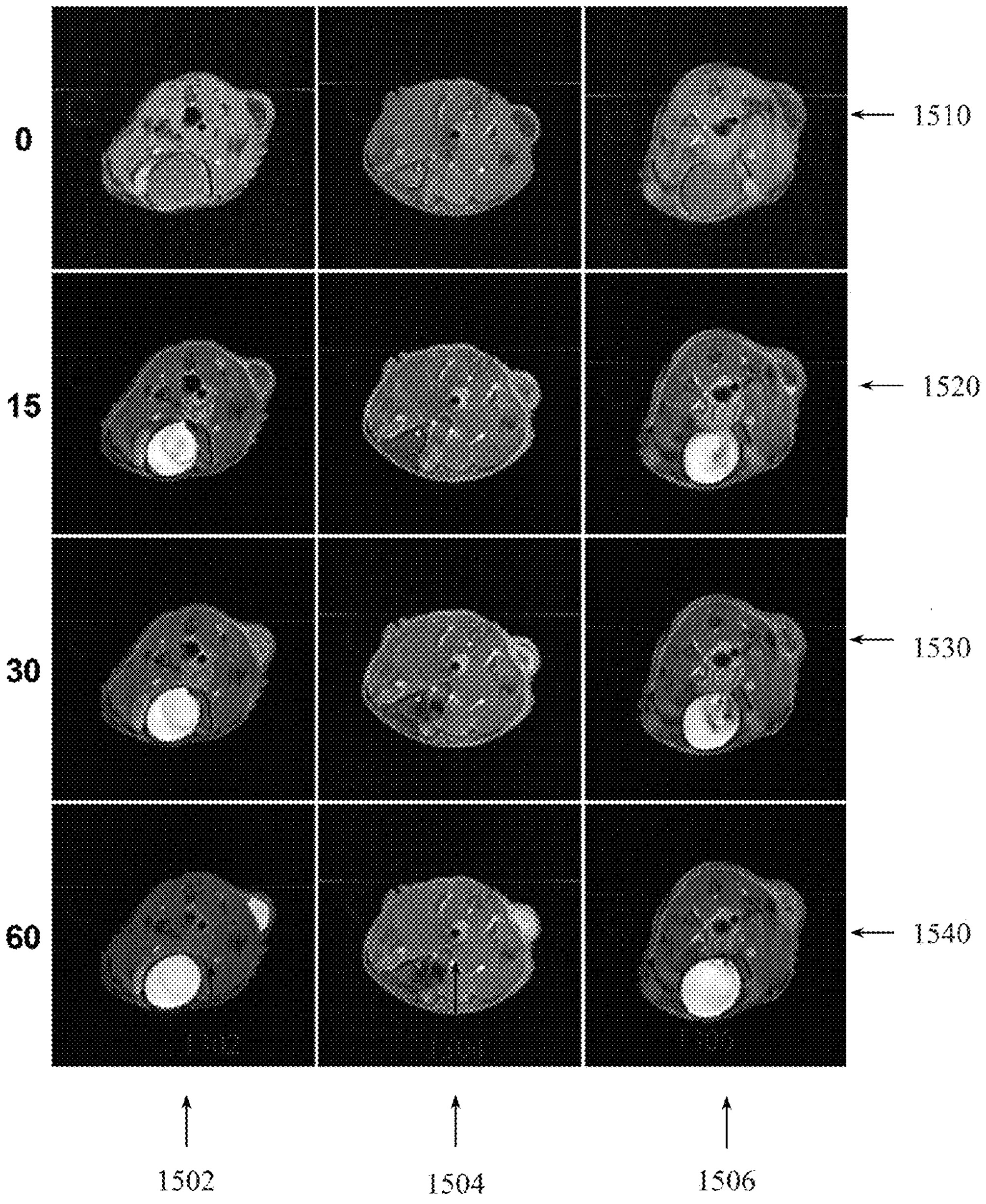
FIG. 15 illustrates maps of percent change in T1 relaxation time.

FIG. 15 illustrates maps of percent change in T1 relaxation time for flank tumors overlaid onto axial T1-weighted images plotted at pre-contrast (0 minutes) (row 1510); 15 minutes post-injection (row 1520); 30 minutes post-injection (row 1530); and 60 minutes post-injection (row 1540). Column 1502 has the maps for Optimark™. Column 1504 has the maps for scrambled and column 1506 has the maps for SBK2. The percent change in T1 values demonstrate that the agent SBK2-Tris-(Gd-DOTA)$_3$ is retained in the tumor for a longer period of time than either Optimark™ or scrambled-Tris-(Gd-DOTA)$_3$ agents.

Figure 16:
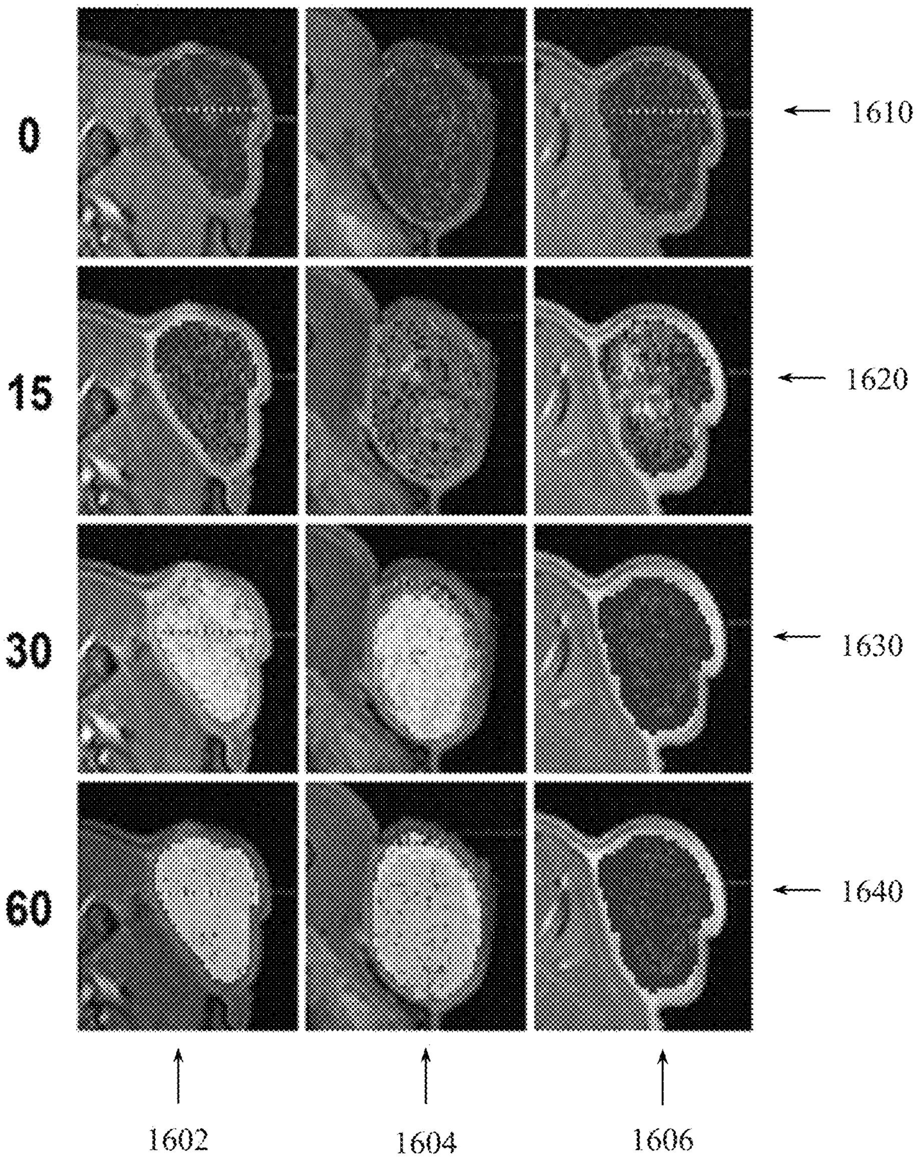
FIG. 16 illustrates maps of percent change in T1 relaxation time.

FIG. 16 also illustrates maps representing the percent change in T1 values. Column 1602 has the maps for Optimark™. Column 1604 has the maps for scrambled and column 1606 has the maps for SBK2. The percent change in T1 values indicates that the tumors of mice at pre-contrast (0 minutes) (row 1610); 15 minutes post-injection (row 1620); 30 minutes post-injection (row 1630); and 60 minutes post-injection (row 1640) show SBK2-Tris-(Gd-DOTA)$_3$ is retained for a much longer period of time than Optimark™ and scrambled-Tris-(Gd-DOTA)$_3$ agents even in larger tumors. Note also that the T1 changes at 30 minutes and 60 minutes for the SBK2-Tris-(Gd-DOTA)$_3$ agent are uniformly distributed throughout the tumor while the non-specific agents show rim enhancement typical of conventional agents.

Figure 17:
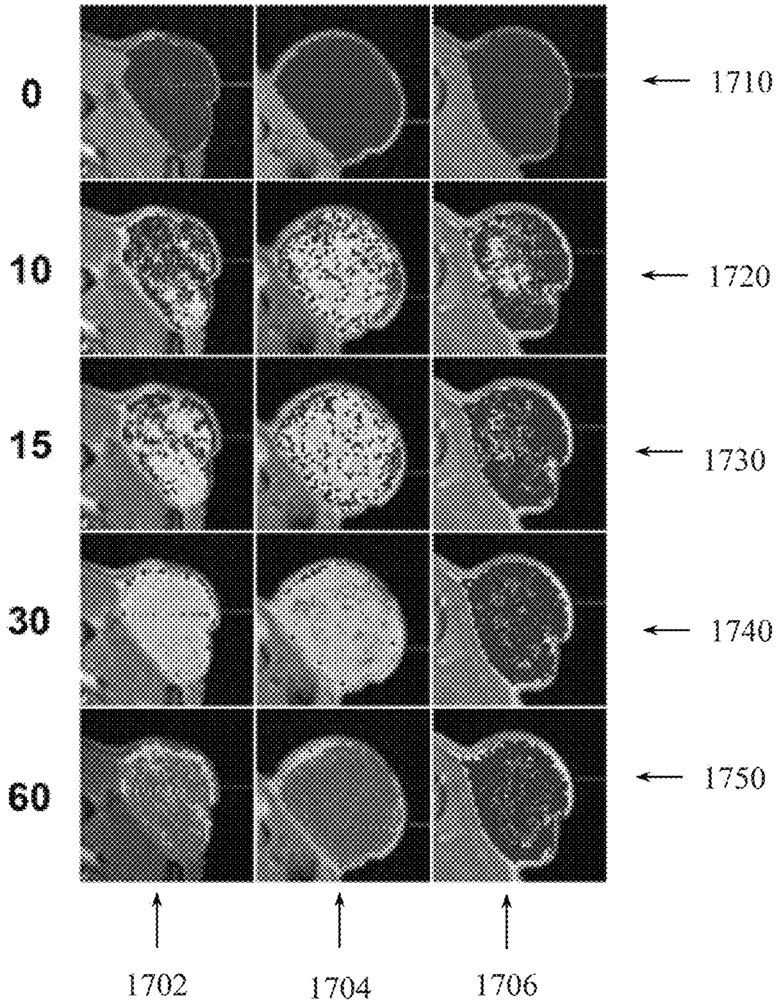
FIG. 17 illustrates gadolinium (Gd) concentration maps in tumor of animals treated with different contrast agents.

FIG. 17 illustrates gadolinium concentrations in tumor of animals treated with different contrast agents. Column 1702 has the maps for Optimark™. Column 1704 has the maps for scrambled and column 1706 has the maps for SBK2. Maps of gadolinium concentration are overlaid onto axial T1-weighted images plotted at pre-contrast (0 minutes) (row 1710); 10 minutes post-injection (row 1720); 15 minutes post-injection (row 1730); 30 minutes post-injection (row 1740); and 60 minutes post-injection (row 1750). Consistent with T1 map values observed for the non-specific contrast agents, Gd concentrations are highest at 10 and 15 minutes in tumors of animals treated with Optimark™ and scrambled-Tris-(Gd-DOTA)$_3$, and then rapidly decrease at later time points. Gd concentration in tumor of the animal receiving SBK2-Tris-(Gd-DOTA)$_3$ remains at near peak levels at 60 minutes indicating retention of the agent in the tumor. Gd concentrations in tumors of animals treated with Optimark™ and scrambled-Tris-(Gd-DOTA)$_3$ are highest at 10 and 15 minutes after injection and then decline. In contrast, the Gd concentration in tumors of animals treated with SBK2-Tris-(Gd-DOTA)$_3$ persist at approximately 0.08 mM from 10 to 60 min. Gd concentrations calculated in control muscle regions were substantially lower than those in tumors.

Figure 18:
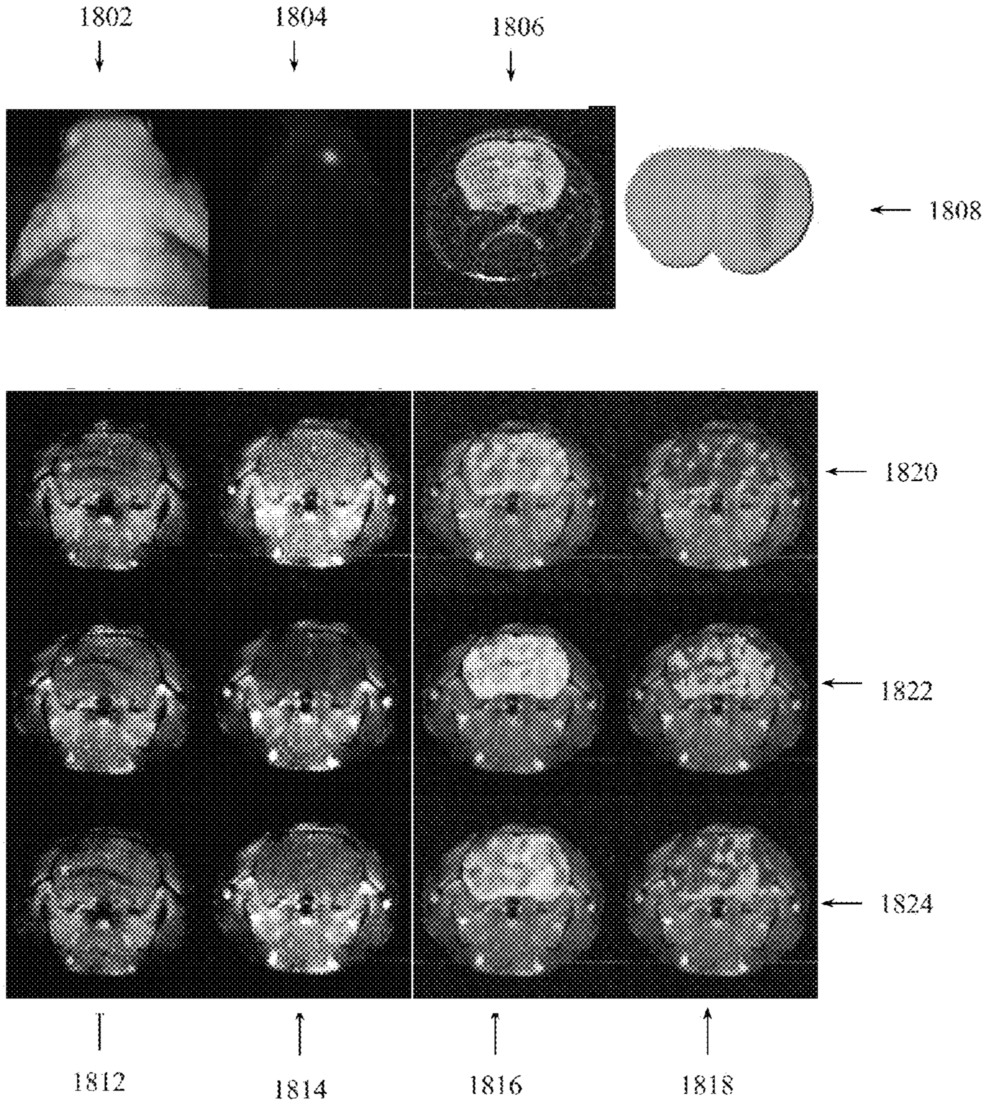
FIG. 18 illustrates T1 weighted imaging and T1 mapping of a glioma tumor.

FIG. 18 illustrates the results of evaluating tumor enhancement using T1-weighted imaging compared to quantitative T1 mapping. Representative bright-field and fluorescent images of athymic mice bearing GFP-positive Gli36Δ5 glioma tumors are illustrated in 1802 and 1804 respectively. A T2-weighted high-resolution image 1806 shows the tumor mass. A hematoxylin and eosin (H&E) stained histological section 1808 shows tumor size, shape, and location.

Column 1812 shows T1-weighted, FLASH acquired, images of an orthotopic Gli36Δ5 glioma tumor. Row 1820 shows the image at baseline or pre-agent, before injection of 0.1 mmol/kg Optimark™. Row 1822 shows the image five minutes following the injection when contrast was at a peak. Row 1824 shows the image twenty minutes post-injection when contrast agent clearance had begun. Even following the injection of the contrast agent, there appears to be no apparent tumor enhancement visible in the T1-weighted FLASH images in column 1812. These small tumors were also not readily discernible in the T1-weighted snapshot GRE images in column 1814. The tumor is detectable in the T1 maps in column 1816 and in the Gd concentration maps in column 1818. This is because T1 mapping is a quantitative MR imaging method that yields the absolute T1 relaxation values as opposed to the relative signal intensity values in T1-weighted images.

Column 1814 shows T1-weighted, snapshot GRE acquired images of an orthotopic Gli36Δ5 glioma tumor.

Column 1816 shows normalized T1 maps of the tumor bearing brains overlaid onto T1-weighted images. Column 1818 shows gadolinium concentration maps of the tumor bearing brains overlaid onto T1-weighted images. Row 1820 shows the image before injecting 0.1 mmol/kg of Optimark™. Row 1822 shows the image two and a half minutes following the injection when peak contrast was achieved. Row 1824 shows the image at twenty two and a half minutes post injection when contrast agent clearance had occurred.

High-resolution T2-weighted MR images were acquired to localize the tumor and enable identification of the largest cross-section of tumor on MRI. This section then served as the reference for the position of the T1 slice in FIG. 18. In one embodiment, T2-weighted images may be acquired to facilitate selecting the slices for which T1 mapping will occur. In another embodiment, MRF may be performed to facilitate selecting the slices for which T1 mapping will occur. Despite a priori knowledge of the location of the xenografts of the non-invasive Gli36Δ5 tumors, tumors of the size used in the experiment were not routinely evident in the T1-weighted or T2-weighted images as illustrated in FIGS. 18 and 19.

Figure 19:
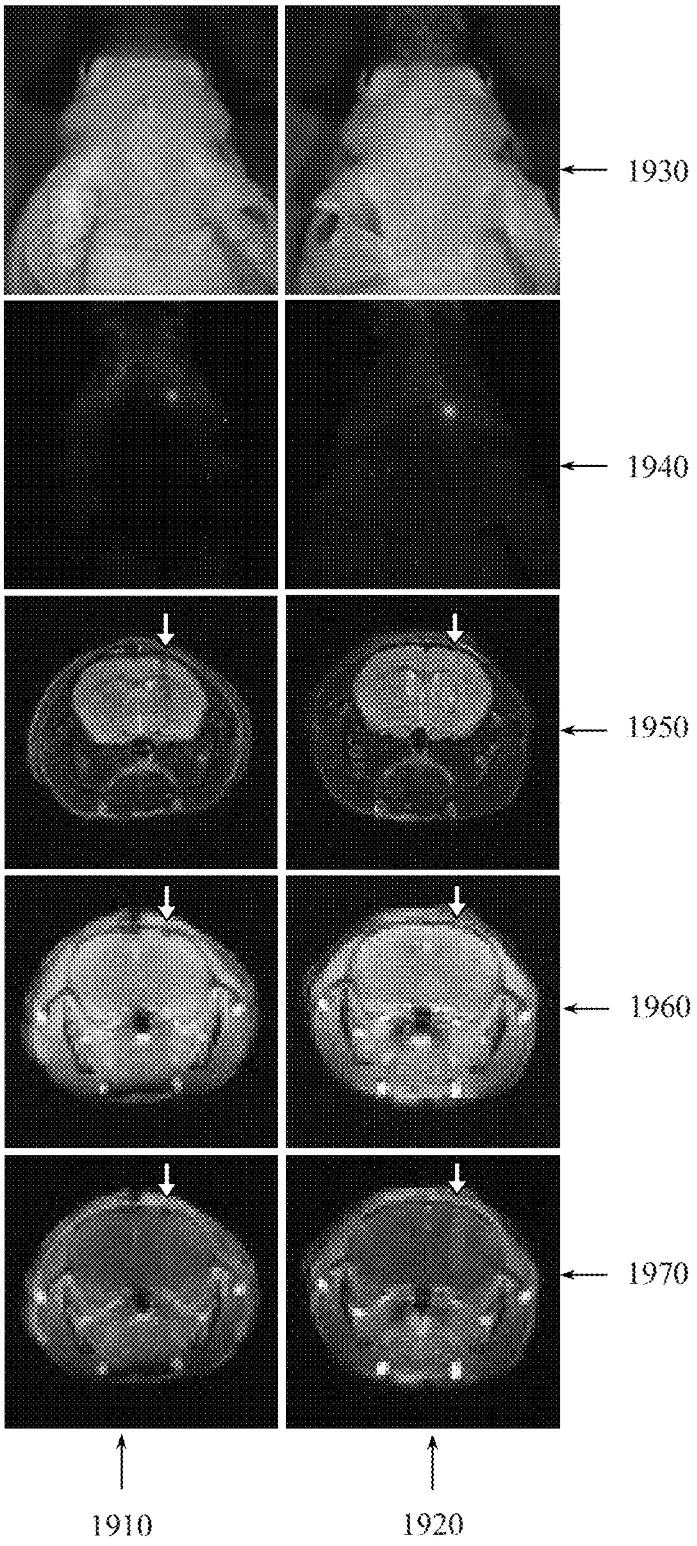
FIG. 19 illustrates tumor enhancement at different dosage levels.

FIG. 19 illustrates the imaging agent Optimark™ producing tumor enhancement of orthotopic glioma tumors in mice at 0.1 and 0.2 mmol/kg. Column 1910 illustrates 0.1 mmol/kg. Column 1920 illustrates 0.2 mmol/kg. Representative bright-field images are illustrated in row 1930. Representative fluorescent images are illustrated in row 1940. Row 1950 illustrates T2-weighted high resolution images. These T2-weighted images show the tumor mass and are co-registered with their corresponding T1-weighted images in rows 1960 and 1970. Row 1960 illustrates the T1-weighted images of orthotopic Gli36Δ5 glioma tumors before injection of contrast agents. Row 1970 illustrates the T1-weighted images at a time of maximum contrast following intravenous administration. Glioma cells are clearly visible in the fluorescent images but not in the T2-weighted images. Tumor masses are also not visible in the baseline or pre-agent T1 maps. However, tumor masses are clearly visible in the post-agent T1 maps.

Figure 20:
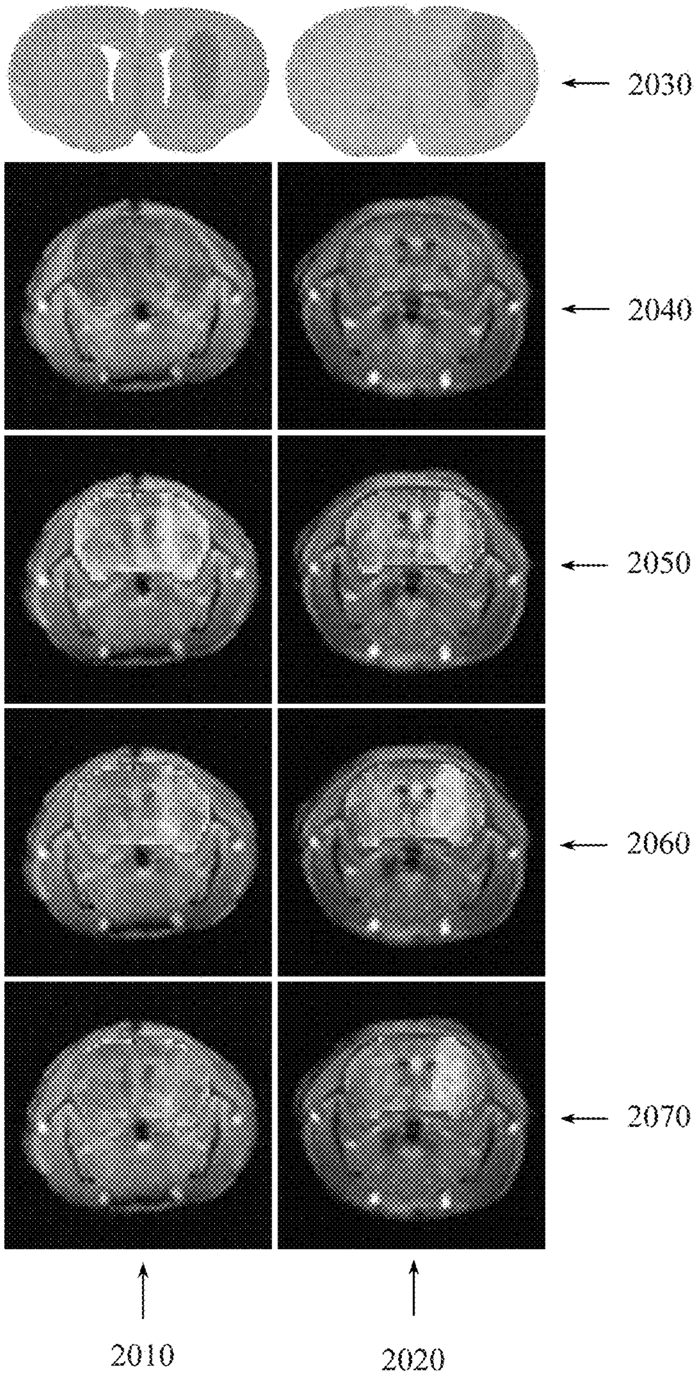
FIG. 20 illustrates quantitative parametric maps.

FIG. 20 illustrates quantitative parametric maps that compare tumor detection ability at 0.1 versus 0.2 mmol/kg dose of the imaging agent. Column 2010 illustrates 0.1 mmol/kg. Column 2020 illustrates 0.2 mmol/kg. Representative normalized T1 maps are shown at baseline or pre-agent (row 2040) at 5 minutes post-agent (row 2050), at 15 minutes post-agent (row 2060), and at 30 minutes post-agent (row 2070) for the two doses. Representative H&E stained histological sections for each mouse are also shown in row 2030 to verify tumor size and shape and to facilitate qualitative comparisons to the tumor enhancement observed in the normalized T1 maps. The 0.1 mmol/kg dose of Optimark™ resulted in a modest decrease in normalized T1 values at 5 minutes. At 15 minutes, the normalized T1 value exhibits recovery towards baseline or pre-agent due to the Optimark™ clearance. By 30 minutes, there is no distinction between T1 value of normal brain and tumor with the 0.1 mmol/kg dose. The 0.2 mmol/kg dose of Optimark™ caused a larger decrease in normalized T1 values compared to 0.1 mmol/kg at 5 minutes. By 15 minutes, the normalized T1 values begin to recover and there is moderate enhancement observed beyond the initial tumor borders seen at 5 minutes. This moderate enhancement likely represents the full extent of the tumor within the 1.5 mm slice. At 30 minutes, a weak distinction remains between normalized T1 values of normal brain and tumor.

Figure 21:
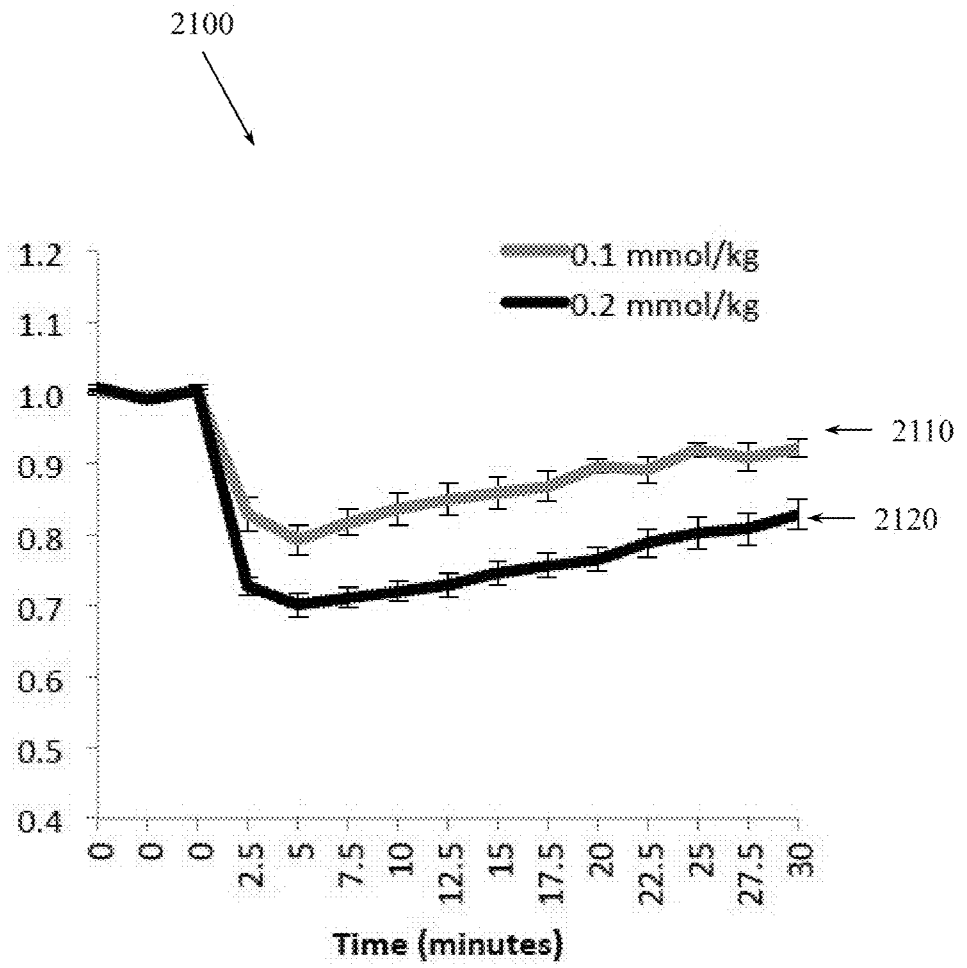
FIG. 21 illustrates mean normalized T1 values.

FIG. 21 compares mean normalized T1 values in brain tumors over time. Comparison of mean normalized T1 values in graph 2100 demonstrates that both the 0.1 mmol/kg dose represented by line 2110 and the 0.2 mmol/kg dose represented by line 2120 exhibited peak enhancement in the tumors at 5 minutes and then steadily returned to baseline or pre-agent values over the next 30 minutes. The 0.2 mmol/kg dose of Optimark™ had a larger and statistically significant decrease ($p<0.00005$ to $p<0.005$ depending on the time point) in normalized T1 values at all time points compared to the 0.1 mmol/kg dose.

Figure 22:
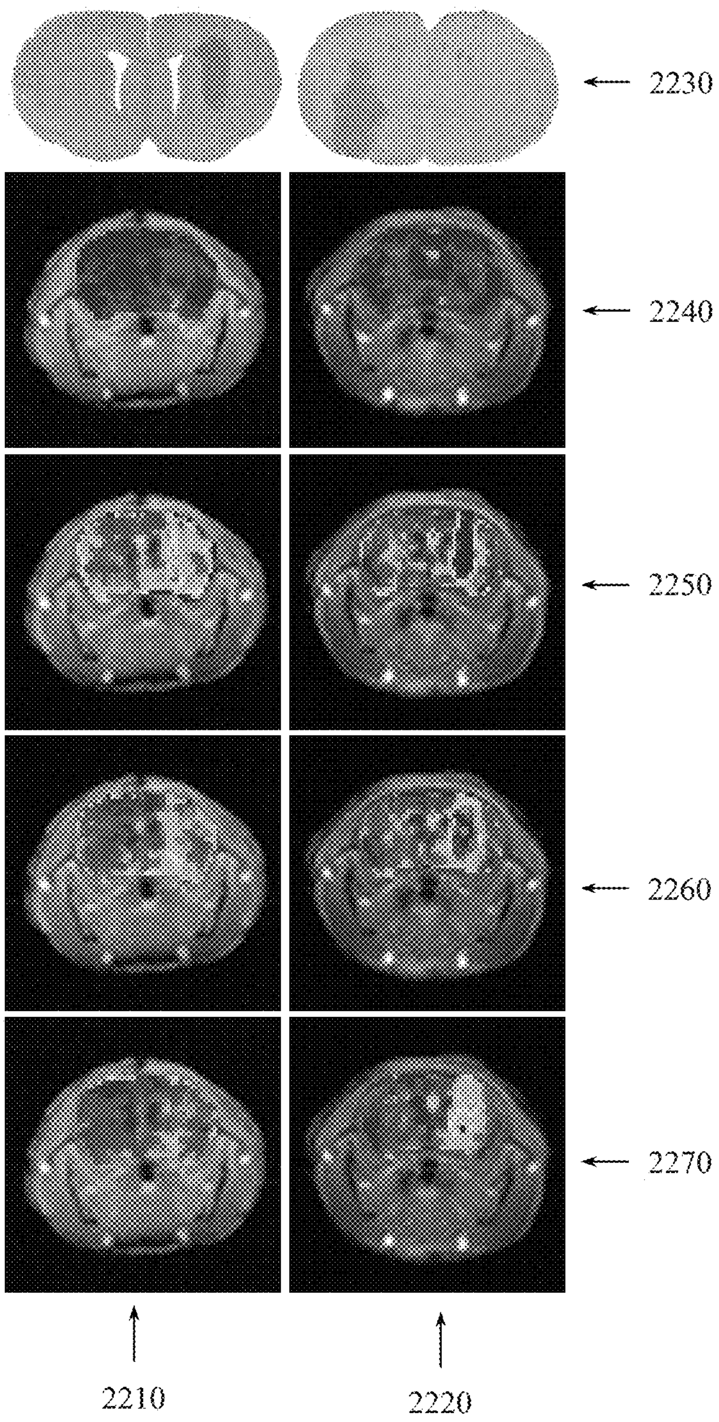
FIG. 22 illustrates Gd concentration maps.

FIG. 22 illustrates gadolinium concentration maps of glioma bearing mice injected with 0.1 mmol/kg (column 2210) and 0.2 mmol/kg (column 2220) doses of Optimark™. The 0.2 mmol/kg dose results in a greater concentration of gadolinium compared to the 0.1 mmol/kg dose. Representative H&E stained histological sections shown in row 2230 show tumor size, shape, and location. Gadolinium concentration maps of the tumor bearing brains are overlaid onto T1-weighted images at baseline or pre-agent (row 2240), at 5 minutes (row 2250), at 15 minutes (row 2260), and at 30 minutes (row 2270) post-agent. These images show that Gd concentration maps facilitate not only evaluating contrast enhancement but also visualizing tumor location. Similar to the normalized T1 maps, gadolinium accumulates beyond the initial contrast area up to five minutes but then declines over time.

Figure 23:
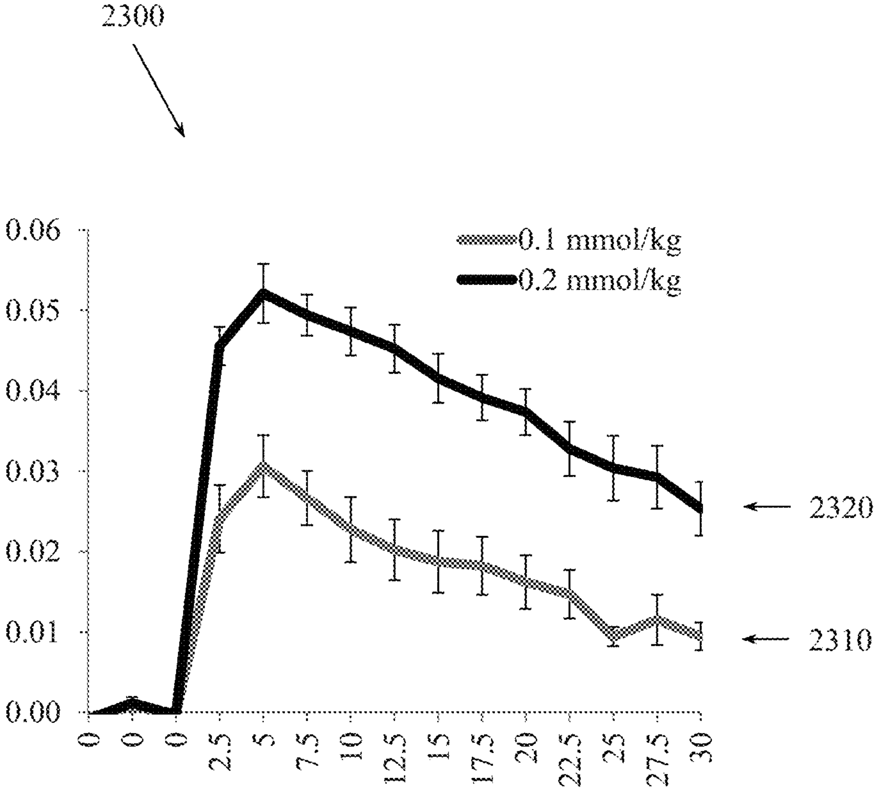
FIG. 23 illustrates Gd concentration values.

FIG. 23 compares Gd concentration over time. Graph 2300 illustrates mean Gd concentrations in the tumor before and after intravenous administration of 0.1 (line 2310) or 0.2 mmol/kg (line 2320) Optimark™ in cohorts of nu/nu athymic mice bearing orthotopic glioma tumors. Data is plotted as means+/−standard error. The mean tumor Gd concentration was measured at baseline or pre-agent and after contrast agent injection was measured every 2.5 minutes for 30 minutes. The graph demonstrates how Gd concentrations are significantly different between the 0.1 and 0.2 mmol/kg doses.

The optimal time to observe the effects of the non-specific imaging agents Optimark™ and other agents (e.g., Omnisan™) is between four to eight minutes post injection. This short period of time may not provide adequate opportunities to acquire enough data and to acquire data of different types that will facilitate improving conventional systems. The optimal time to observe the effects of the specific agent SBK2 is much longer, and may extend out to two hours, which provides opportunities to acquire a larger and more varied data set.

Figure 24:
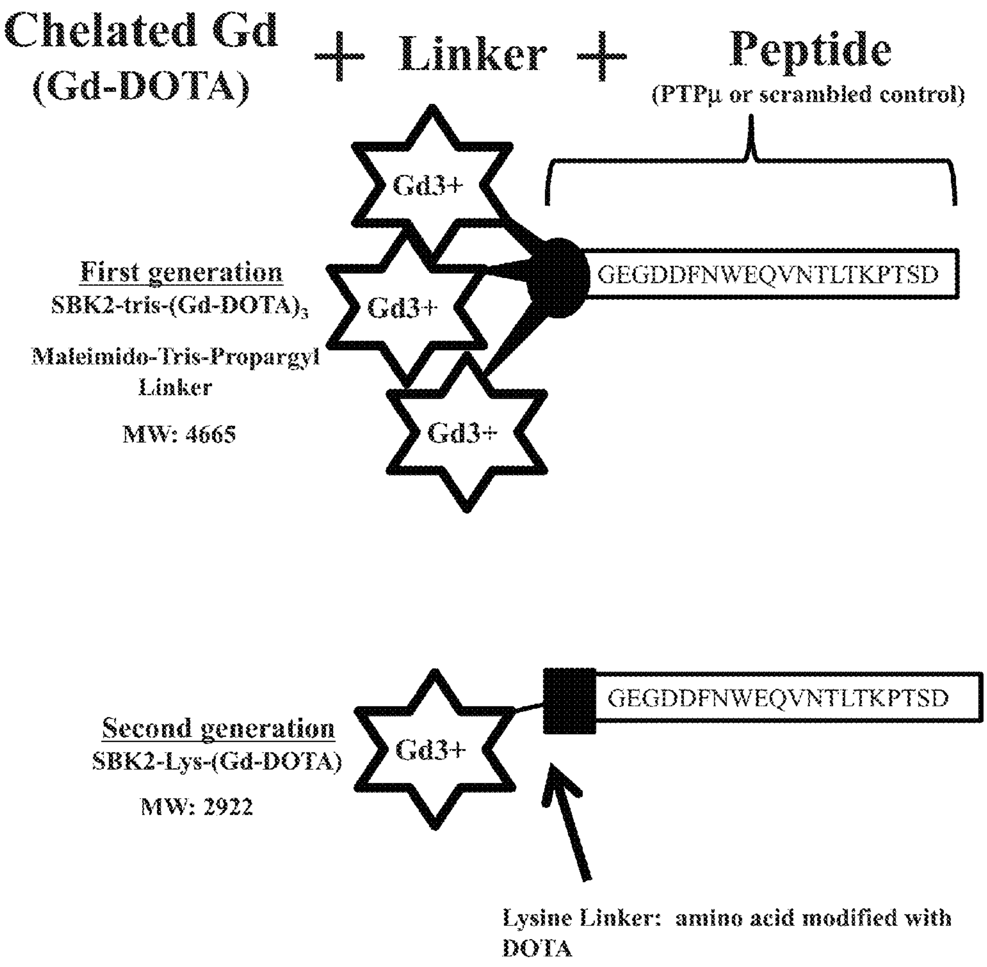
FIG. 24 illustrates the first and second generation SBK2 contrast agents.

FIG. 24 illustrates the differences between first and second generation SBK2 contrast agents. The first generation agents were scrambled-Tris-$(Gd\text{-}DOTA)_3$, or SBK2-Tris-$(Gd\text{-}DOTA)_3$ contrast agents. They contained a maleimido-tris-propargyl linker that permitted complexation with three Gd ions. The second generation agents are scrambled-Lys-(Gd-DOTA), or SBK2-Lys-(Gd-DOTA) contrast agents. These agents use the amino acid lysine coupled to DOTA and contain a single Gd.

Figure 25:
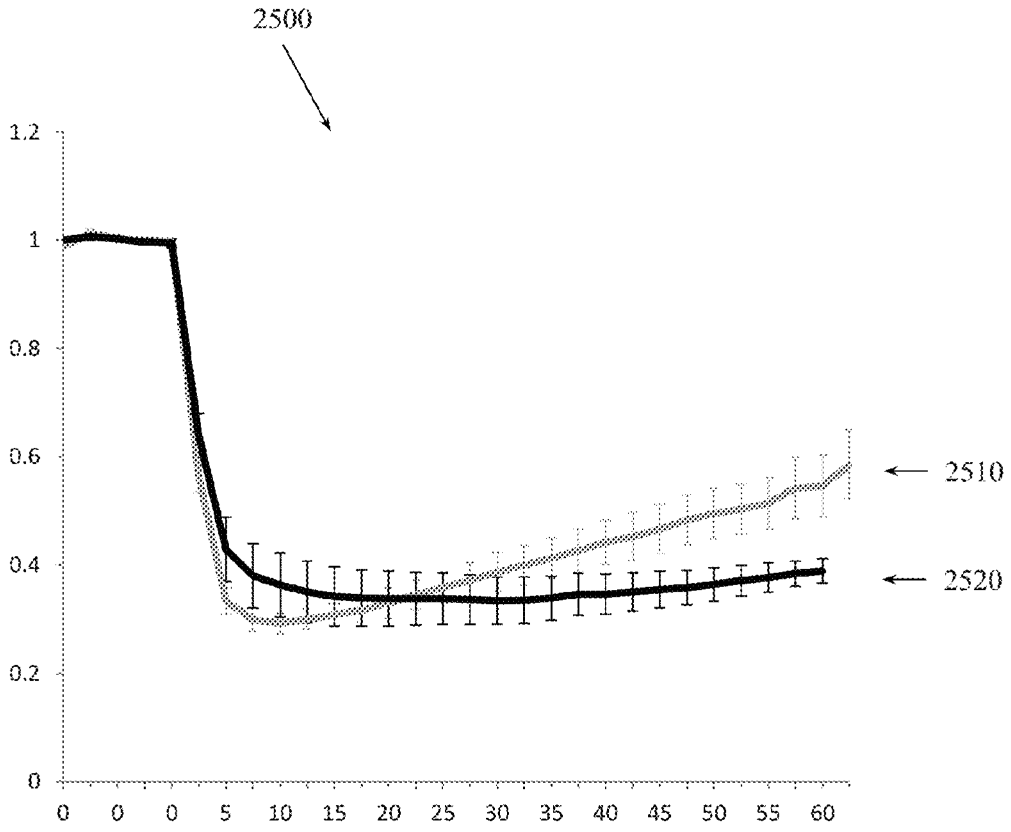
FIG. 25 illustrates mean normalized T1 values from Lys-DOTA contrast agents.

FIG. 25 illustrates mean tumor normalized T1 values following intravenous administration of scrambled-Lys-(Gd-DOTA), or SBK2-Lys-(Gd-DOTA) contrast agents in cohorts of nu/nu athymic mice bearing glioma flank tumors administered at a dose of 0.2 mmol Gd/kg. These agents contain a single Gd compared to previous versions with three Gd chelates. The slope for SBK2 is illustrated in line 2420. The slope for scrambled is illustrated in lines 2410. Note the sustained decrease in normalized T1 for SBK2-Lys-(Gd-DOTA) as well as the significant difference in slope due to agent clearance between the non-specific agents compared to SBK2-Lys-(Gd-DOTA), which showed the highest retention. FIG. 25 illustrates mean tumor normalized T1 values at baseline or pre-agent and after agent injection measured every 2.5 minutes for 62.5 minutes. Normalized T1 values are significantly different between SBK2-Lys-(Gd-DOTA) and scrambled-Lys-(Gd-DOTA) from 30-62.5 minutes.

Figure 26:
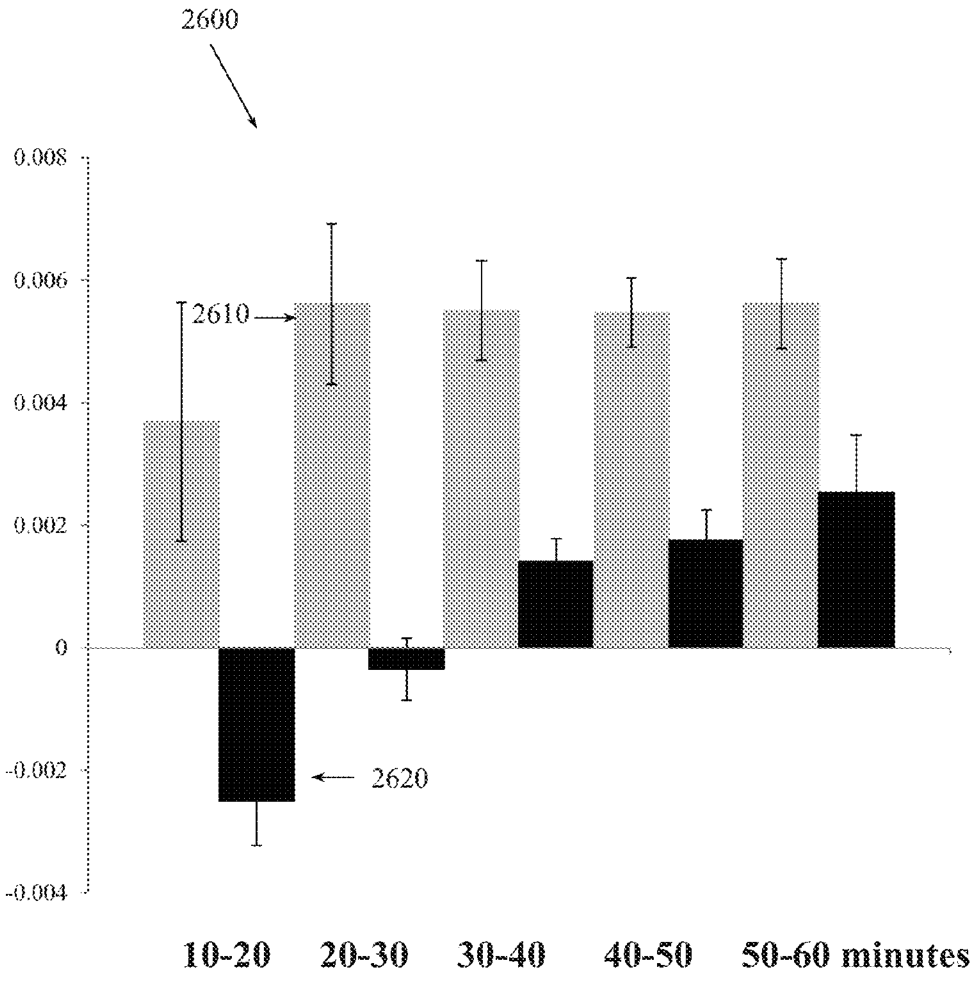
FIG. 26 illustrates slope values from Lys-DOTA contrast agents at 0.2 mmol/kg.

FIG. 26 illustrates tumor slope values following intravenous administration of scrambled-Lys-(Gd-DOTA), or SBK2-Lys-(Gd-DOTA) contrast agents in cohorts of nu/nu athymic mice bearing glioma flank tumors administered at a dose of 0.2 mmol Gd/kg. These agents contain a single Gd compared to previous versions with three Gd chelates. The slope for SBK2 is illustrated in line 2520. The slope for scrambled is illustrated in lines 2510. Note the negative slope values for SBK2-Lys-(Gd-DOTA) compared to the non-specific agent scrambled-Lys-(Gd-DOTA). FIG. 25 illustrates tumor slope values after agent injection measured in ranges of 10-20, 20-30, 30-40, 40-50 and 50-60 minutes. Slope values are significantly different between SBK2-Lys-(Gd-DOTA) and scrambled-Lys-(Gd-DOTA) in all time ranges. Importantly, there is a negative slope for 10-20 and the 20-30 time ranges for SBK2-Lys-(Gd-DOTA).

Figure 27:
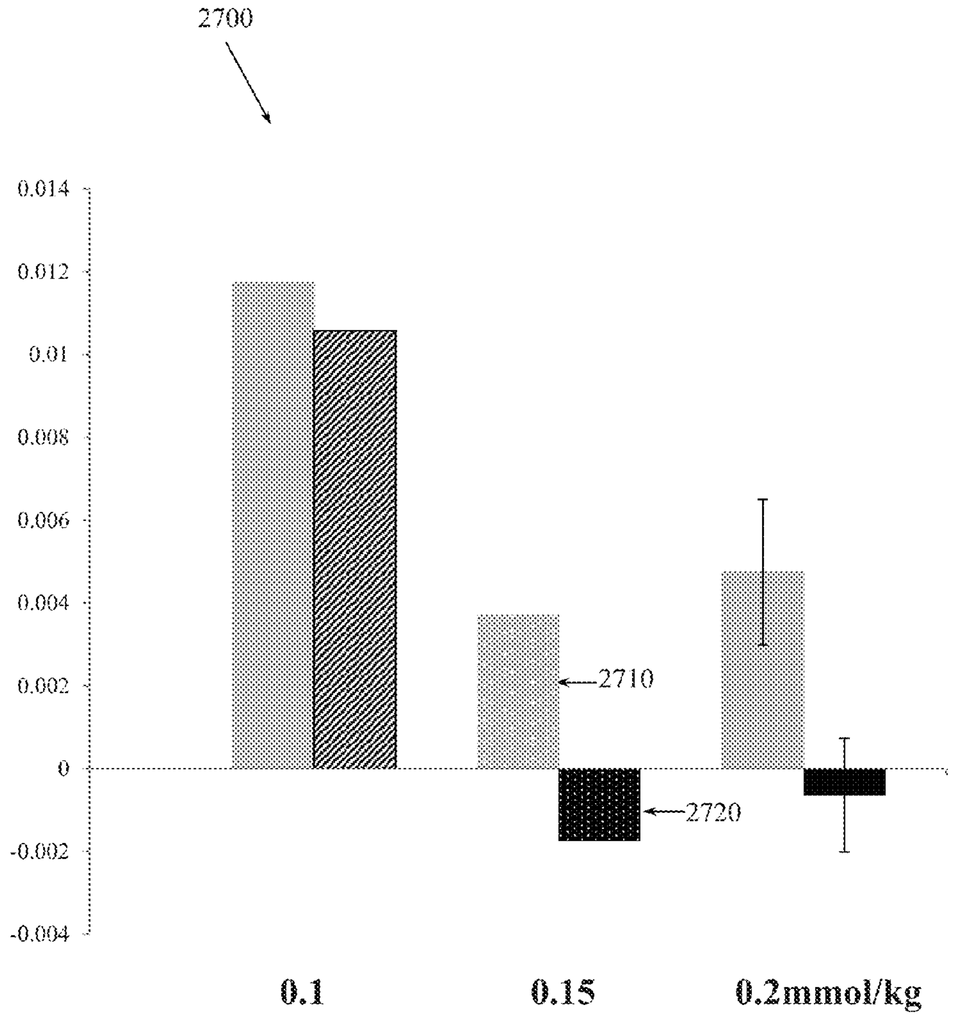
FIG. 27 illustrates slope values from different doses of Lys-DOTA contrast agents (0.1, 0.15, 0.2 mmol/kg).

FIG. 27 illustrates tumor slope values following intravenous administration of scrambled-Lys-(Gd-DOTA), or SBK2-Lys-(Gd-DOTA) contrast agents in cohorts of nu/nu athymic mice bearing glioma flank tumors administered at a dose of 0.1, 0.15 and 0.2 mmol Gd/kg. These agents contain a single Gd compared to previous versions with three Gd chelates. The slope for SBK2 is illustrated in line 2620. The slope for scrambled is illustrated in lines 2610. Note the negative slope values for SBK2-Lys-(Gd-DOTA) compared to the non-specific agent scrambled-Lys-(Gd-DOTA) at the 0.15 and 0.2 mmol/kg concentrations. FIG. 27 illustrates tumor slope values after agent injection measured in the range of 15-30 minutes.

FIGS. 1, 8-9, 12-17 and 25-27 demonstrate that contrast agent concentration is higher in tumor than in control areas of muscle, that contrast agent concentration remains at peak levels for at least sixty minutes using SBK2, and that contrast agent concentration begins to diminish after peak within thirty minutes using scrambled, Optimark™, or Prohance™. FIGS. 1, 8-9, 12-17 and 25-27 also demonstrate that SBK2 uniformly recognizes the entire tumor while the non-specific agents do not uniformly recognize the entire tumor. The combination of these facts proves that quantitative T1 mapping and the generation of parametric maps facilitate improved detection of brain tumors (FIGS. 18-23) compared to conventional T1-weighted imaging.

To the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing at least one of A, "at least one of B, and at least one of C" will be employed.

To the extent that the term "includes" or "including" is employed in the detailed description or the claims, it is intended to be inclusive in a manner similar to the term "comprising" as that term is interpreted when employed as a transitional word in a claim.

References to one embodiment", an embodiment", one example", and an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. A method, comprising:

acquiring a nuclear magnetic resonance (NMR) data set from a volume during a period of time in which a change in T1 in the volume due to a molecular imaging agent remains within ninety percent of a peak change in spin-lattice relaxation time (T1) in the volume due to the molecular agent, wherein the molecular imaging agent binds to a tumor in the volume and changes T1 in the tumor; and detecting a tumor that is less than the size of a voxel in the volume based on identifying characteristic changes in T1 over time using quantitative T1 relaxation time mapping of the NMR data set.

2. The method of claim 1, comprising:

displaying an image of the tumor, where the image is reconstructed from the NMR data set.

3. The method of claim 1, where acquiring the NMR data from the volume comprises:

acquiring a set of pre-agent NMR data from the volume before the molecular imaging agent is introduced into the volume; and acquiring one or more sets of post-agent NMR data during a period of time during which a change in T1 caused by the molecular imaging agent in the volume remains within at least 90% of a peak change in T1 caused by the molecular imaging agent in the volume, where the period of time is at least fifteen minutes.

4. The method of claim 3, where the period of time is at least thirty minutes.

5. The method of claim 3, where the period of time is at least sixty minutes.

6. The method of claim 3, where identifying characteristic changes in T1 over time is based on quantitative T1 relaxation time mapping applied to the one or more sets of post-agent NMR data indicating that a concentration of at least 0.08 mM is reached in the volume and that a concentration of Gd of at least 0.07 mM is maintained for the period of time in the volume.

7. The method of claim 3, where identifying characteristic changes in T1 over time is based on quantitative T1 relaxation time mapping applied to the one or more sets of post-agent NMR data and the set of pre-agent NMR data, where the quantitative T1 relaxation time mapping indicates a concentration of at least 0.08 mM is reached and that a concentration of Gd of at least 0.07 mM is maintained for the period of time.

8. The method of claim 2, comprising acquiring another set of NMR data from the volume after the molecular imaging agent has been introduced into the volume;

reconstructing a T2 weighted image from the another set of NMR data; and selecting a sub-volume of the volume from which one or more sets of NMR data will be acquired based, at least in part, on the T2 weighted image.

9. The method of claim 3, where acquiring members of the one or more sets of NMR data includes acquiring data using a T1 based acquisition approach, a T2 based acquisition approach, or a proton density acquisition approach.

10. The method of claim 9 further comprising acquiring at least one member of the sets of data using magnetic resonance fingerprinting.

11. The method of claim 9 further comprising;

producing a combined data set by adding together two or more members of the one or more sets of NMR data, by subtracting two or more members of the one or more sets of data from each other, by ANDing together two or more members of the one or more sets of data, by ORing together two or more members of the one or more sets of NMR data, or by XORing together two or more members of the sets of NMR data, and reconstructing an image of the tumor from the combined data set.

12. The method of claim 3, where acquiring members of the one or more sets of data includes acquiring data in a coronal plane, acquiring data in a sagittal plane, and acquiring data in a transverse plane.

13. The method of claim 12, where the image of the tumor is a three dimensional image produced from data acquired in a coronal plane, a sagittal plane, and a transverse plane.

14. The method of claim 6, comprising calculating gadolinium concentration maps from the one or more sets of post-agent NMR data.

15. The method of claim 14, further comprising calculating gadolinium concentration per voxel according to:

$$\Delta\left(\frac{1}{T_1}\right) = \frac{1}{T_{1,post}} - \frac{1}{T_{1,pre}} = r1 \times [G_d]$$

where T1 is the measured T1, r1 is the relaxivity value, and

[Gd] is the gadolinium concentration.

16. The method of claim 3, where a first portion of the one or more sets of data is acquired while the volume is positioned in a first magnetic resonance apparatus operating with a first main magnetic field strength and where a second portion of the one or more sets of data is acquired while the volume is positioned in a second, different magnetic resonance apparatus operating with a second, magnetic field strength different than the first main magnetic field strength.

17. The method of claim 1, where detecting the tumor that is less than the size of a voxel in the volume based on identifying characteristic changes in T1 over time using quantitative T1 relaxation time mapping of the NMR data set includes analyzing slope values of the molecular imaging agent.

18. The method of claim 1, wherein the molecular imaging agent is SBK2 conjugated to Lys-Gd.

19. The method of claim 1, wherein the molecular imaging agent is SBK2 conjugated to Lys-DOTA that is a Gd chelate.

20. A non-transitory computer-readable medium having instructions stored thereon that when executed by a processor cause the processor to carry out steps comprising:

acquiring a baseline value for a magnetic resonance (MR) parameter of a region in a sample while the sample is not exposed to a molecular imaging agent that affects the MR parameter in the sample;

acquiring a series of quantitative values for the MR parameter, wherein the series of quantitative values for the MR parameter were acquired from the sample over a period of time during which the molecular imaging agent affects the MR parameter to within 90% of a peak influence of the molecular imaging agent on the MR parameter, the period of time being at least fifteen minutes, and wherein values in the series of values are a function of the concentration of the molecular imaging agent in the region;

comparing changes in the MR parameter over the period of time to produce a quantitative map of the MR parameter; and producing and displaying a quantitative map of the concentration of the molecular imaging agent in the volume from the series of quantitative values, where the baseline value and the series of quantitative values are a function of nuclear magnetic resonance (NMR) experienced in the sample as excited by an NMR apparatus, where acquiring the series of quantitative values include acquiring two or more different data sets, where at least one member of the two or more different data sets includes data from NMR signals associated with spin-lattice relaxation time (T1), where at least one member of the two or more different data sets includes data from NMR signals associated with spin-spin relaxation time (T2), and where at least one member of the two or more different data sets includes data from NMR signals associated with proton density.

21. The non-transitory computer-readable medium of claim 20, where the baseline value or the series of quantitative values are acquired using magnetic resonance fingerprinting.

22. The non-transitory computer-readable medium of claim 20, where the MR parameter is spin-lattice relaxation time (T1), spin-spin relaxation time (T2), or proton density.

23. The non-transitory computer-readable medium of claim 20, further comprising characterizing the region with respect to the presence of a pathological state as a function of the quantitative maps.

24. The non-transitory computer-readable medium of claim 20, where the region is bounded by a voxel used in magnetic resonance imaging (MRI) reconstruction, and where the voxel size is less than 1×1×1 $mm^3$.

25. The non-transitory computer-readable medium of claim 20, where the sample is a human tissue and the target material is a protein associated with a disease.

26. The non-transitory computer-readable medium of claim 25, where the disease is cancer.

27. The non-transitory computer-readable medium of claim 26, where the protein is tyrosine phosphatase μ.

28. The non-transitory computer-readable medium of claim 20, where the molecular imaging agent recognizes the target material by binding to the target material in a protein: protein interaction.

29. The non-transitory computer-readable medium of claim 28, where the molecular imaging agent is a first peptide conjugated to a contrast agent.

30. The non-transitory computer-readable medium of claim 29, where the first peptide is SBK2 and where the contrast agent is gadolinium.

31. The non-transitory computer-readable medium of claim 29, where the first peptide is SBK2 and where the contrast agent is a nanoparticle.

32. The non-transitory computer-readable medium of claim 20, where the series of quantitative values are acquired using magnetic resonance fingerprinting.

33. The non-transitory computer-readable medium of claim 20, wherein the process is further caused to carry out steps comprising:

producing a combined data set from two or more members of the two or more data sets by applying an operator to corresponding members of the two or more data sets;

reconstructing an image from the combined data set; and presenting the image.

34. The non-transitory computer-readable medium of claim 20, where acquiring the series of quantitative values includes acquiring data in a sagittal plane, acquiring data in a coronal plane, and acquiring data in a transverse plane, and the method comprising reconstructing a three dimensional image of the tumor from the data acquired in the sagittal plane, the data acquired in the coronal plane, and the data acquired in the transverse plane.

35. The non-transitory computer-readable medium of claim 20, where comparing changes in the MR parameter over the period of time to produce the quantitative map of the MR parameter includes analyzing slope values of the molecular imaging agent.

36. An apparatus for use with a magnetic resonance (MR) apparatus, comprising:

a processor;

a memory;

a set of operational modules; and an interface to connect the processor, the memory, and the set of operational modules, the set of operational modules comprising:

a first operational module that measures a baseline spin-lattice relaxation time (T1) in a sample before a molecular imaging agent that changes T1 in a glioblastoma is presented to the sample;

a second operational module that acquires a set of quantitative T1 measurements in the sample for a period of time exceeding thirty minutes during which the sample is experiencing a change in T1 of at least 95% of the peak change in T1 caused by the presence of the molecular imaging agent in the glioblastoma;

a third operational module that produces a T1 relaxation time map that illustrates changes in T1 in the sample over time; and a fourth operational module that generates a signal upon identifying that a glioblastoma is present in the sample, where the identifying is performed as a function of changes in spin-lattice relaxation time (T1) between the baseline T1 and the set of T1 measurements and characteristic changes in T1 in the set of T1 measurements, a fifth operational module that controls switching between different NMR signal acquisition approaches including T1 signal acquisition only, spin-spin relaxation time (T2) signal acquisition only, proton density signal acquisition only, and magnetic resonance fingerprinting based simultaneous acquisition of T1 signal, T2 signal, and proton density signal.

37. The apparatus of claim 36, where the molecular imaging agent is SBK2 conjugated to Tris-$(Gd\text{-}DOTA)_3$.

38. The apparatus of claim 37, where the second operational module acquires the set of quantitative T1 measurements using magnetic resonance fingerprinting.

39. The apparatus of claim 36, comprising a sixth operational module that produces an image from the T1 relaxation time map.

40. The apparatus of claim 36, where the fifth operational module produces a combined data set by applying one or more data manipulating operations to data acquired using the different NMR signal acquisition approaches.

41. The apparatus of claim 40, where the fifth operational module reconstructs a magnetic resonance image from the combined data set and displays the magnetic resonance image.

42. The apparatus of claim 36, wherein the molecular imaging agent is SBK2 conjugated to Lys-Gd.

43. The apparatus of claim 36, wherein the molecular imaging agent is SBK2 conjugated to Lys-DOTA that is a Gd chelate.

44. A method, comprising:

acquiring, using a magnetic resonance (MR) apparatus, a nuclear magnetic resonance (NMR) data set from a volume including a tumor during a period of time in which a change in spin-lattice relaxation time (T1) in the volume due to a molecular imaging agent remains within ninety percent of a peak change in T1 in the volume due to the molecular agent, wherein the molecular imaging agent is configured to bind to the tumor in the volume and change T1 in the tumor;

performing a quantitative T1 relaxation time mapping of the NMR data set;

using the quantitative T1 relaxation time mapping of the NMR data set, identifying characteristic changes in T1 over time indicative of signal from a tumor; and generating a report indicating the presence of the tumor in regions less than the size of a voxel in the volume.

45. The method of claim 44, wherein generating the report further includes displaying an image of the tumor, where the image is reconstructed from the NMR data set.

46. The method of claim 44, where acquiring the NMR data from the volume using the MR apparatus comprises:

acquiring a set of pre-agent NMR data from the volume before the molecular imaging agent is introduced into the volume; and acquiring one or more sets of post-agent NMR data during a period of time during which a change in T1 caused by the molecular imaging agent in the volume remains within at least 90% of a peak change in T1 caused by the molecular imaging agent in the volume, where the period of time is at least fifteen minutes.

47. The method of claim 46, where the period of time is at least thirty minutes.

48. The method of claim 46, where identifying characteristic changes in T1 over time is based on quantitative T1 relaxation time mapping applied to the one or more sets of post-agent NMR data indicating that a concentration of at least 0.08 mM is reached in the volume and that a concentration of Gd of at least 0.07 mM is maintained for the period of time in the volume.

49. The method of claim 46, where identifying characteristic changes in T1 over time is based on quantitative T1 relaxation time mapping applied to the one or more sets of post-agent NMR data and the set of pre-agent NMR data, where the quantitative T1 relaxation time mapping indicates a concentration of at least 0.08 mM is reached and that a concentration of Gd of at least 0.07 mM is maintained for the period of time.

50. The method of claim 46, comprising acquiring another set of post-agent NMR data from the volume after the molecular imaging agent has been introduced into the volume;

reconstructing a T2 weighted image from the another set of post-agent NMR data; and selecting a sub-volume of the volume from which one or more sets of post-agent NMR data will be acquired based, at least in part, on the T2 weighted image.

51. The method of claim 50, where acquiring members of the one or more sets of post-agent NMR data includes acquiring data using a T1 based acquisition approach, a T2 based acquisition approach, or a proton density acquisition approach.

52. The method of claim 51, further comprising acquiring at least one member of the sets of post-agent data using a magnetic resonance fingerprinting process.

53. The method of claim 51, further comprising:

producing a combined data set by adding together two or more members of the one or more sets of post-agent NMR data, by subtracting two or more members of the one or more sets of post-agent NMR data from each other, by ANDing together two or more members of the one or more sets of post-agent NMR data, by ORing together two or more members of the one or more sets of post-agent NMR data, or by XORing together two or more members of the one or more sets of post-agent NMR data, and reconstructing an image of the tumor from the combined data set.

54. The method of claim 46, comprising calculating gadolinium concentration maps from the one or more sets of post-agent NMR data.

55. The method of claim 54, further comprising calculating gadolinium concentration per voxel according to:

$$\Delta\left(\frac{1}{T_1}\right) = \frac{1}{T_{1,post}} - \frac{1}{T_{1,pre}} = r1 \times [G_d]$$

where T1 is the measured T1, r1 is the relaxivity value, and

[Gd] is the gadolinium concentration.

56. The method of claim 44, where identifying characteristic changes in T1 over time indicative of signal from the tumor includes analyzing slope values of the molecular imaging agent.

57. The method of claim 44, wherein the molecular imaging agent is SBK2 conjugated to Lys-Gd.

58. The method of claim 44, wherein the molecular imaging agent is SBK2 conjugated to Lys-DOTA that is a Gd chelate.

* * * * *